(12) United States Patent
Pothini et al.

(10) Patent No.: US 12,411,148 B2
(45) Date of Patent: Sep. 9, 2025

(54) INSTRUMENTS, DEVICES AND CONSUMABLES FOR USE IN A WORKFLOW OF A SMART MOLECULAR ANALYSIS SYSTEM

(71) Applicant: LIFE TECHNOLOGIES CORPORATION, Carlsbad, CA (US)

(72) Inventors: Shakila Pothini, Union City, CA (US); Hardeep Sangha, Union City, CA (US); Marc Haberstroh, San Jose, CA (US); Puneet Suri, Redwood City, CA (US); Damien Luk, San Francisco, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 17/459,090

(22) Filed: Aug. 27, 2021

(65) Prior Publication Data

US 2022/0091143 A1 Mar. 24, 2022

Related U.S. Application Data

(63) Continuation of application No. 16/262,823, filed on Jan. 30, 2019, now Pat. No. 11,112,416.

(Continued)

(51) Int. Cl.
*G01N 35/00* (2006.01)
*B01L 3/00* (2006.01)
(Continued)

(52) U.S. Cl.
CPC ...... *G01N 35/00732* (2013.01); *B01L 3/5085* (2013.01); *B01L 3/54* (2013.01);
(Continued)

(58) Field of Classification Search
CPC .. F04C 18/16; F04C 2240/403; F04C 23/008; F04C 29/0007; F04C 29/042;
(Continued)

(56) References Cited

U.S. PATENT DOCUMENTS 3,549,406 A 12/1970 Ambusk
3,888,759 A 6/1975 Elson et al.
(Continued)

FOREIGN PATENT DOCUMENTS

CN 103221827 A 7/2013
CN 106714687 A 5/2017
(Continued)

OTHER PUBLICATIONS

US 7,165,720 B2, 01/2007, Linton et al. (withdrawn)
(Continued)

*Primary Examiner* — Jennifer Wecker
*Assistant Examiner* — Jonathan Bortoli

(57) ABSTRACT

A system for performing a molecular analysis workflow includes a reaction holder or a reaction substrate, such as a multi-well reaction plate, with a reaction holder/substrate RFID tag, and/or a reagent container with a reagent container RFID tag, and an instrument and/or device that includes an RFID reader/writer operable to read and/or write information to and from the reaction holder/substrate RFID tag and/or the reagent container RFID tag. The reaction holder/substrate RFID tag and the reagent container RFID tag can be utilized separately or together to send and receive and store information, for example, for a workflow of a molecular analysis, such as a polymerase chain reaction (PCR).

13 Claims, 16 Drawing Sheets

Related U.S. Application Data

(60) Provisional application No. 62/624,080, filed on Jan. 30, 2018.

(51) Int. Cl.
| | |
|---|---|
| *G06K 7/10* | (2006.01) |
| *G06K 19/07* | (2006.01) |
| *G16H 10/40* | (2018.01) |
| *G16H 40/67* | (2018.01) |
| *G16H 50/20* | (2018.01) |

(52) U.S. Cl.
CPC ........ *B01L 3/545* (2013.01); *G01N 35/00871* (2013.01); *G06K 7/10366* (2013.01); *G06K 19/0723* (2013.01); *B01L 2200/14* (2013.01); *B01L 2200/16* (2013.01); *B01L 2300/021* (2013.01); *B01L 2300/022* (2013.01); *B01L 2300/023* (2013.01); *B01L 2300/024* (2013.01); *B01L 2300/025* (2013.01); *B01L 2300/0627* (2013.01); *B01L 2300/0829* (2013.01); *G01N 2035/00742* (2013.01); *G01N 2035/00782* (2013.01); *G01N 2035/00811* (2013.01); *G01N 2035/00851* (2013.01); *G01N 2035/00881* (2013.01); *G16H 10/40* (2018.01); *G16H 40/67* (2018.01); *G16H 50/20* (2018.01)

(58) Field of Classification Search
CPC .............. F25B 2400/13; F25B 2400/23; F25B 2500/07; F25B 2600/021; F25B 2600/0253; F25B 2700/193; F25B 49/005; F25B 49/025; F25B 9/002; Y02B 30/70; B01L 2200/14; B01L 2200/16; B01L 2300/021; B01L 2300/022; B01L 2300/023; B01L 2300/024; B01L 2300/025; B01L 2300/0627; B01L 2300/0829; B01L 3/5085; B01L 3/54; B01L 3/545; G01N 2035/00742; G01N 2035/00782; G01N 2035/00811; G01N 2035/00851; G01N 2035/00881; G01N 35/00732; G01N 35/00871; G06K 19/0723; G06K 7/10366; G16H 10/40; G16H 40/67; G16H 50/20
See application file for complete search history.

(56) References Cited

U.S. PATENT DOCUMENTS

| | | |
|---|---|---|
| 3,960,499 A | 6/1976 | White |
| 4,006,069 A | 2/1977 | Hiratsuka et al. |
| 4,072,639 A | 2/1978 | Yamaguchi et al. |
| 4,094,759 A | 6/1978 | Ruhenstroth-Bauer et al. |
| 4,246,092 A | 1/1981 | Perry et al. |
| 4,411,490 A | 10/1983 | Daniel |
| 4,415,418 A | 11/1983 | Turre et al. |
| 4,415,428 A | 11/1983 | Nochumson et al. |
| 4,418,098 A | 11/1983 | Maistrovich |
| 4,548,869 A | 10/1985 | Ogawa et al. |
| 4,548,870 A | 10/1985 | Ogawa et al. |
| 4,569,794 A | 2/1986 | Smith et al. |
| 4,579,783 A | 4/1986 | Ogawa et al. |
| 4,600,641 A | 7/1986 | Ogawa et al. |
| 4,717,667 A | 1/1988 | Provonchee |
| 4,718,998 A | 1/1988 | Ogawa et al. |
| 4,737,259 A | 4/1988 | Ogawa et al. |
| 4,908,112 A | 3/1990 | Pace |
| 4,915,811 A | 4/1990 | Yamamoto et al. |
| 4,929,972 A | 5/1990 | Anderson et al. |
| 5,055,517 A | 10/1991 | Shorr et al. |
| 5,128,412 A | 7/1992 | Miyasaka et al. |
| 5,190,632 A | 3/1993 | Fujimiya et al. |
| 5,212,299 A | 5/1993 | Smith |
| 5,219,923 A | 6/1993 | Shorr |
| 5,225,212 A | 7/1993 | Martin et al. |
| 5,238,651 A | 8/1993 | Chuba |
| 5,252,294 A | 10/1993 | Kroy et al. |
| 5,306,468 A | 4/1994 | Anderson et al. |
| 5,384,028 A | 1/1995 | Ito |
| 5,395,619 A | 3/1995 | Zalipsky et al. |
| 5,397,449 A | 3/1995 | Zewert et al. |
| 5,455,344 A | 10/1995 | Harper et al. |
| 5,476,016 A | 12/1995 | Fedorka-Cray et al. |
| 5,498,324 A | 3/1996 | Yeung et al. |
| 5,585,069 A | 12/1996 | Zanzucchi et al. |
| 5,641,400 A | 6/1997 | Kaltenbach et al. |
| 5,641,626 A | 6/1997 | Dumais et al. |
| 5,641,634 A | 6/1997 | Mandecki |
| 5,670,226 A | 9/1997 | Yoshizawa et al. |
| 5,672,416 A | 9/1997 | Radola et al. |
| 5,681,437 A | 10/1997 | Black et al. |
| 5,700,429 A | 12/1997 | Buehler et al. |
| 5,741,462 A | 4/1998 | Nova et al. |
| 5,751,629 A | 5/1998 | Nova et al. |
| 5,764,892 A | 6/1998 | Cain et al. |
| 5,770,455 A | 6/1998 | Cargill et al. |
| 5,779,868 A | 7/1998 | Parce et al. |
| 5,790,727 A | 8/1998 | Dhadwal et al. |
| 5,817,472 A | 10/1998 | Hardham et al. |
| 5,840,877 A | 11/1998 | Kozulic |
| 5,851,370 A | 12/1998 | Maracas et al. |
| 5,851,488 A | 12/1998 | Saul et al. |
| 5,859,587 A | 1/1999 | Alicot et al. |
| 5,874,214 A | 2/1999 | Nova et al. |
| 5,882,679 A | 3/1999 | Needham |
| 5,883,376 A | 3/1999 | Roesch et al. |
| 5,885,432 A | 3/1999 | Hooper et al. |
| 5,910,287 A | 6/1999 | Cassin et al. |
| 5,925,562 A | 7/1999 | Nova et al. |
| 5,949,049 A | 9/1999 | McCarrick et al. |
| 5,953,682 A | 9/1999 | McCarrick et al. |
| 5,954,931 A | 9/1999 | Maracas et al. |
| 5,962,834 A | 10/1999 | Markman |
| 5,990,238 A | 11/1999 | Dizio et al. |
| 5,993,627 A | 11/1999 | Anderson et al. |
| 6,013,168 A | 1/2000 | Arai |
| 6,017,434 A | 1/2000 | Simpson et al. |
| 6,017,624 A | 1/2000 | Delgado et al. |
| 6,025,129 A | 2/2000 | Nova et al. |
| 6,025,159 A | 2/2000 | Liu et al. |
| 6,027,695 A | 2/2000 | Oldenburg et al. |
| 6,031,458 A | 2/2000 | Jacobsen et al. |
| 6,060,022 A | 5/2000 | Pang et al. |
| 6,071,394 A | 6/2000 | Cheng et al. |
| 6,085,603 A | 7/2000 | Riekkinen |
| 6,090,251 A | 7/2000 | Sundberg et al. |
| 6,090,255 A | 7/2000 | Riley et al. |
| 6,094,137 A | 7/2000 | Rasch et al. |
| 6,103,199 A | 8/2000 | Bjornson et al. |
| 6,112,152 A | 8/2000 | Tuttle |
| 6,123,821 A | 9/2000 | Anderson et al. |
| 6,132,685 A | 10/2000 | Kercso et al. |
| 6,136,173 A | 10/2000 | Anderson et al. |
| 6,139,709 A | 10/2000 | Scott |
| 6,140,146 A | 10/2000 | Brady et al. |
| 6,147,662 A | 11/2000 | Grabau et al. |
| 6,149,058 A | 11/2000 | Albaret |
| 6,171,780 B1 | 1/2001 | Pham et al. |
| 6,187,250 B1 | 2/2001 | Champagne |
| 6,201,474 B1 | 3/2001 | Brady et al. |
| 6,206,292 B1 | 3/2001 | Robertz et al. |
| 6,211,781 B1 | 4/2001 | McDonald |
| 6,219,137 B1 | 4/2001 | Vo-Dinh |
| 6,245,206 B1 | 6/2001 | Anderson et al. |
| 6,251,516 B1 | 6/2001 | Bonner et al. |
| 6,258,606 B1 | 7/2001 | Kovacs |
| 6,259,367 B1 | 7/2001 | Klein |
| 6,277,630 B1 | 8/2001 | Brophy et al. |
| 6,278,794 B1 | 8/2001 | Parekh et al. |
| 6,280,590 B1 | 8/2001 | Cheng et al. |
| 6,297,727 B1 | 10/2001 | Nelson, Jr. |

(56) References Cited

U.S. PATENT DOCUMENTS

| | | |
|---|---|---|
| 6,300,141 B1 | 10/2001 | Segal et al. |
| 6,317,028 B1 | 11/2001 | Valiulis |
| 6,317,208 B1 | 11/2001 | Hirosawa |
| 6,319,668 B1 | 11/2001 | Nova et al. |
| 6,329,139 B1 | 12/2001 | Nova et al. |
| 6,352,854 B1 | 3/2002 | Nova et al. |
| 6,359,444 B1 | 3/2002 | Grimes |
| 6,361,950 B1 | 3/2002 | Mandecki |
| 6,372,428 B1 | 4/2002 | Nova et al. |
| 6,376,187 B1 | 4/2002 | Mandecki |
| 6,387,623 B1 | 5/2002 | Mandecki |
| 6,416,714 B1 | 7/2002 | Nova et al. |
| 6,417,010 B1 | 7/2002 | Cargill et al. |
| 6,429,016 B1 | 8/2002 | McNeil |
| 6,454,924 B2 | 9/2002 | Jedrzejewski et al. |
| 6,458,259 B1 | 10/2002 | Parce et al. |
| 6,483,434 B1 | 11/2002 | UmiKer |
| 6,520,544 B1 | 2/2003 | Mitchell et al. |
| 6,521,111 B1 | 2/2003 | Amshey et al. |
| 6,535,129 B1 | 3/2003 | Petrick |
| 6,541,211 B1 | 4/2003 | Patek et al. |
| 6,586,143 B1 | 7/2003 | Tan et al. |
| 6,637,473 B2 | 10/2003 | Ganz et al. |
| 6,652,812 B1 | 11/2003 | Vartiainen et al. |
| 6,670,609 B2 | 12/2003 | Franzen et al. |
| 6,677,852 B1 | 1/2004 | Landt |
| 6,686,158 B2 | 2/2004 | Mandecki |
| 6,699,437 B1 | 3/2004 | Astle |
| 6,726,820 B1 | 4/2004 | Frazier |
| 6,733,728 B1 | 5/2004 | Mimura et al. |
| 6,734,797 B2 | 5/2004 | Shanks et al. |
| 6,806,050 B2 | 10/2004 | Zhou et al. |
| 6,824,738 B1 | 11/2004 | Neeper et al. |
| 6,824,740 B1 | 11/2004 | Sheldon et al. |
| 6,847,912 B2 | 1/2005 | Forster |
| 6,858,439 B1 | 2/2005 | Xu et al. |
| 6,867,048 B2 | 3/2005 | Kovacs |
| 6,881,314 B1 | 4/2005 | Wang et al. |
| 6,887,362 B2 | 5/2005 | Huang et al. |
| 6,889,468 B2 | 5/2005 | Bedingham et al. |
| 6,906,797 B1 | 6/2005 | Kao et al. |
| 6,917,291 B2 | 7/2005 | Allen |
| 6,928,353 B2 | 8/2005 | Finley et al. |
| 6,934,836 B2 | 8/2005 | Strand et al. |
| 6,935,560 B2 | 8/2005 | Andreasson et al. |
| 6,942,778 B1 | 9/2005 | Jalali et al. |
| 6,953,834 B1 | 10/2005 | DeJong |
| 6,982,640 B2 | 1/2006 | Lindsay et al. |
| 6,986,836 B2 | 1/2006 | Panattoni et al. |
| 7,053,777 B2 | 5/2006 | Allen |
| 7,061,379 B2 | 6/2006 | Chen et al. |
| 7,091,864 B2 | 8/2006 | Veitch et al. |
| 7,113,131 B2 | 9/2006 | Burke |
| 7,118,708 B2 | 10/2006 | Mordekhay |
| 7,142,987 B2 | 11/2006 | Eggers |
| 7,153,403 B2 | 12/2006 | Alpenfels et al. |
| 7,187,286 B2 | 3/2007 | Morris et al. |
| 7,298,885 B2 | 11/2007 | Green et al. |
| 7,338,811 B2 | 3/2008 | Lai |
| 7,361,260 B2 | 4/2008 | Amshey et al. |
| 7,382,258 B2 | 6/2008 | Oldham et al. |
| 7,390,458 B2 | 6/2008 | Burow et al. |
| 7,663,487 B2 | 2/2010 | Morris et al. |
| 7,880,617 B2 | 2/2011 | Morris et al. |
| 8,049,623 B2 | 11/2011 | Morris et al. |
| 8,059,623 B2 | 11/2011 | Gandham et al. |
| 8,400,304 B2 | 3/2013 | Morris et al. |
| 8,665,071 B2 | 3/2014 | Morris et al. |
| 8,669,848 B2 | 3/2014 | Morris et al. |
| 8,669,849 B2 | 3/2014 | Morris et al. |
| 9,019,079 B2 | 4/2015 | Morris et al. |
| 2001/0008390 A1 | 7/2001 | Berquist et al. |
| 2001/0021356 A1 | 9/2001 | Konrad |
| 2002/0018733 A1 | 2/2002 | Kapplein et al. |
| 2002/0030598 A1 | 3/2002 | Dombrowski et al. |
| 2002/0052238 A1 | 5/2002 | Muroi |
| 2002/0076819 A1 | 6/2002 | Bowman et al. |
| 2002/0077886 A1 | 6/2002 | Chung |
| 2002/0090320 A1 | 7/2002 | Burow et al. |
| 2002/0094515 A1 | 7/2002 | Erlach et al. |
| 2002/0098472 A1 | 7/2002 | Erlach et al. |
| 2002/0098598 A1 | 7/2002 | Coffen et al. |
| 2002/0111551 A1 | 8/2002 | Erlach et al. |
| 2002/0114739 A1 | 8/2002 | Weigl et al. |
| 2003/0017082 A1 | 1/2003 | Van et al. |
| 2003/0058110 A1 | 3/2003 | Rich |
| 2003/0072676 A1 | 4/2003 | Fletcher-Haynes et al. |
| 2003/0087446 A1 | 5/2003 | Eggers |
| 2003/0087455 A1 | 5/2003 | Eggers et al. |
| 2003/0087955 A1 | 5/2003 | Miller et al. |
| 2003/0124539 A1 | 7/2003 | Warrington et al. |
| 2003/0151028 A1 | 8/2003 | Lawrence et al. |
| 2003/0183683 A1 | 10/2003 | Stewart |
| 2003/0190608 A1 | 10/2003 | Blackburn |
| 2003/0196897 A1 | 10/2003 | Alpenfels et al. |
| 2003/0211012 A1 | 11/2003 | Bergstrom et al. |
| 2003/0217925 A1 | 11/2003 | Alpenfels et al. |
| 2003/0231986 A1 | 12/2003 | Kocher |
| 2004/0029109 A1 | 2/2004 | Lai |
| 2004/0029310 A1 | 2/2004 | Bernds et al. |
| 2004/0094949 A1 | 5/2004 | Savagian et al. |
| 2004/0100380 A1 | 5/2004 | Lindsay et al. |
| 2004/0100415 A1 | 5/2004 | Veitch et al. |
| 2004/0101966 A1 | 5/2004 | Davis et al. |
| 2004/0121432 A1 | 6/2004 | Klein et al. |
| 2004/0124437 A1 | 7/2004 | Doudoumopolous |
| 2004/0131505 A1 | 7/2004 | Koeda |
| 2004/0133092 A1 | 7/2004 | Kain |
| 2004/0136873 A1 | 7/2004 | Meier |
| 2004/0155754 A1 | 8/2004 | Fischer et al. |
| 2004/0161795 A1 | 8/2004 | Marto |
| 2004/0172160 A1 | 9/2004 | O'Dougherty et al. |
| 2004/0173508 A1 | 9/2004 | Deursen et al. |
| 2004/0173781 A1 | 9/2004 | Lawrence et al. |
| 2004/0175515 A1 | 9/2004 | Lawrence et al. |
| 2004/0175548 A1 | 9/2004 | Lawrence et al. |
| 2004/0175550 A1 | 9/2004 | Lawrence et al. |
| 2004/0193449 A1 | 9/2004 | Wildman et al. |
| 2004/0195102 A1 | 10/2004 | Panattoni et al. |
| 2004/0202577 A1 | 10/2004 | McNeil et al. |
| 2004/0203047 A1 | 10/2004 | Caren et al. |
| 2004/0222297 A1 | 11/2004 | Dearing et al. |
| 2005/0159982 A1 | 7/2005 | Showalter et al. |
| 2005/0191670 A1* | 9/2005 | Stylli ............... B01L 9/523 435/7.1 |
| 2005/0205673 A1* | 9/2005 | Morris ............. G01N 35/00732 235/385 |
| 2005/0219039 A1 | 10/2005 | Allen |
| 2005/0242963 A1 | 11/2005 | Oldham et al. |
| 2005/0276728 A1 | 12/2005 | Muller-Cohn et al. |
| 2006/0099567 A1 | 5/2006 | Muller-Cohn et al. |
| 2006/0173750 A1 | 8/2006 | Naley et al. |
| 2006/0190185 A1 | 8/2006 | Ford et al. |
| 2006/0199196 A1 | 9/2006 | O'Banion et al. |
| 2006/0283945 A1 | 12/2006 | Excoffier et al. |
| 2007/0120685 A1 | 5/2007 | Morris et al. |
| 2007/0202538 A1 | 8/2007 | Glezer et al. |
| 2008/0024301 A1 | 1/2008 | Fritchie et al. |
| 2008/0235055 A1 | 9/2008 | Mattingly et al. |
| 2008/0237043 A1 | 10/2008 | Amshey et al. |
| 2008/0238627 A1* | 10/2008 | Oldham ............... H02J 7/1423 340/572.1 |
| 2008/0284602 A1 | 11/2008 | Morris et al. |
| 2009/0071829 A1 | 3/2009 | O'Banion et al. |
| 2009/0269800 A1* | 10/2009 | Covey ............... G01N 35/1095 435/287.1 |
| 2010/0075859 A1* | 3/2010 | Garey ................ G01N 33/585 506/13 |
| 2010/0202925 A1* | 8/2010 | Sonnleitner ......... G01N 21/253 422/75 |
| 2010/0209298 A1* | 8/2010 | Kalra ................ G01N 1/312 422/63 |
| 2010/0262379 A1 | 10/2010 | Frazier |
| 2010/0307921 A1 | 12/2010 | Frazier |

(56) References Cited

U.S. PATENT DOCUMENTS

| | | | |
|---|---|---|---|
| 2011/0001609 A1 | 1/2011 | Oldham et al. | |
| 2011/0115633 A1 | 5/2011 | Morris et al. | |
| 2011/0212859 A1* | 9/2011 | O'Banion | C12Q 1/68 |
| | | | 435/235.1 |
| 2011/0227734 A1* | 9/2011 | Ortenzi | G08B 13/1436 |
| | | | 340/568.1 |
| 2012/0145798 A1 | 6/2012 | Morris et al. | |
| 2012/0229262 A1 | 9/2012 | Amor et al. | |
| 2013/0063252 A1 | 3/2013 | Morris et al. | |
| 2013/0217141 A1 | 8/2013 | Lenhard et al. | |
| 2014/0167924 A1* | 6/2014 | Morris | G06K 7/0008 |
| | | | 340/10.6 |
| 2014/0187448 A1 | 7/2014 | O'Banion et al. | |
| 2014/0234181 A1* | 8/2014 | Fritchie | G01N 1/28 |
| | | | 422/521 |
| 2014/0240096 A1 | 8/2014 | Johns et al. | |
| 2015/0064082 A1 | 3/2015 | Morris et al. | |
| 2016/0012208 A1* | 1/2016 | Clinton | G16C 20/20 |
| | | | 702/27 |
| 2016/0016140 A1* | 1/2016 | Jovanovich | B01L 3/502738 |
| | | | 506/40 |
| 2016/0016165 A1 | 1/2016 | Provencher et al. | |
| 2016/0178654 A1* | 6/2016 | Silbert | G01N 1/31 |
| | | | 436/43 |
| 2017/0160298 A1 | 6/2017 | Wakamiya et al. | |
| 2017/0219614 A1 | 8/2017 | Cook et al. | |
| 2017/0336428 A1* | 11/2017 | Kwang | G16H 10/40 |
| 2018/0128806 A1 | 5/2018 | Yamashita et al. | |

FOREIGN PATENT DOCUMENTS

| | | |
|---|---|---|
| DE | 3032069 A1 | 3/1982 |
| DE | 3032071 A1 | 4/1982 |
| DE | 3032069 C2 | 6/1982 |
| DE | 3032070 A1 | 7/1982 |
| DE | 3032071 C2 | 7/1982 |
| DE | 3032070 C2 | 10/1982 |
| EP | 0376611 A2 | 7/1990 |
| EP | 0840115 A2 | 5/1998 |
| EP | 1772736 A1 | 4/2007 |
| EP | 1812605 A2 | 8/2007 |
| EP | 2660607 A1 | 11/2013 |
| JP | H01257255 A | 10/1989 |
| JP | H09111198 A | 4/1997 |
| JP | 2001-188061 A | 7/2001 |
| JP | 2003289566 A | 10/2003 |
| JP | 2004061136 A | 2/2004 |
| JP | 2004093519 A | 3/2004 |
| JP | 2004166555 A | 6/2004 |
| JP | 2004246492 A | 9/2004 |
| JP | 2008519285 A | 6/2008 |
| JP | 2009521686 A | 6/2009 |
| JP | 2011053229 A | 3/2011 |
| JP | 2011-511238 A | 4/2011 |
| JP | 2011203114 A | 10/2011 |
| JP | 2013500496 A | 1/2013 |
| JP | 2015-200668 A | 11/2015 |
| JP | 2017-015713 A | 1/2017 |
| JP | 2017523809 A | 8/2017 |
| KR | 20150110767 A | 10/2015 |
| WO | WO-9608433 A1 | 3/1996 |
| WO | WO-9636436 A1 | 11/1996 |
| WO | WO-9859092 A1 | 12/1998 |
| WO | WO-0147638 A2 | 7/2001 |
| WO | WO-2005040500 A2 | 5/2005 |
| WO | WO-2005113147 A2 | 12/2005 |
| WO | WO-2006060125 A2 | 6/2006 |
| WO | WO-2007121324 A1 * 10/2007 ............ B01L 3/0227 |
| WO | 2013/052318 A1 | 4/2013 |

OTHER PUBLICATIONS

AIM Incorporated: "Radio Frequency Identification RFID," A Basic Primer, The Association of the Automatic Identification and Capture Industry, Pittsburgh, PA, Aug. 23, 2001, pp. 1-17.

Ausubel F.M., et al., "Current Protocols in Molecular Biology," Table of Contents, John Wiley & Sons Inc., 1994-1998, vol. 1, Supplement 63, 12 Pages.

Baines M.G., et al., "Purification of Immunoglobulin G (IgG)," Immunochemical Protocols, Methods in Molecular Biology, The Humana Press, Inc, Totowa, NJ , 1992, Chapter 8, vol. 10, 26 pages.

Barbas C.F., et al., "A companion to Methods in Immunology," Methods, Apr. 1991, vol. 2, pp. 119-124.

Birge R.R., et al., "Biomolecular Electronics: Protein-Based Associative Processors and Volumetric Memories," The Journal of Physical Chemistry B, 1999, vol. 103 (49), pp. 10746-10766.

Birge R.R., "Protein-Based Three Dimensional Memory," American Scientist, Jul.-Aug. 1994, vol. 82, pp. 348-355.

Brush M., "Prepare to Cast Off: A Profile of Precast Acrylamide Gels," The Scientist, vol. 12, No. 15, Jul. 20, 1998, pp. 1-9.

"Certified translation of JP2001188061," Jul. 2001, 9 pages.

Cooper H.M., et al., "Production of Antibodies," Current Protocols in Immunology, Section II, Unit 2.4, 1995, Supplement 13, 9 pages.

"Dupont Nucrel," Acid copolymer resins, Apr. 17, 2008, 2 pages, Retrieved from URL: http://www.dupont.com/industrial-polymers/nucrel/.

Ecker D.J., et al., "Combinatorial Drug Discovery: Which Methods Will Produce the Greatest Value?," Biotechnology, Apr. 13, 1995, vol. 13, pp. 351-360.

Extended European Search Report for Application No. 05851446 mailed Mar. 22, 2012, 8 pages.

Flotte T.R., "Prospects for virus-based gene Therapy for cystic fibrosis," Journal Bioenergetic and Biomembranes, 1993, vol. 92, pp. 37-42.

Fraley, R. et al. "New Generation Liposomes: The Engineering of an Efficient Vehicle for Intracellular Delivery of Nucleic Acids," Trends in Biochemical Sciences, Mar. 1981, vol. 6, pp. 77-80.

Frost P., "Tiny Channels Carved in Plastic Enable Medical Test on a CD," Ohio State Research News, 2000, 3 pages.

Goeddel D.V., "Gene Expression Technology," Methods in Enzymology, Table of Contents, Academic Press, Inc., San Diego, CA, 1990, vol. 185, 7 Pages.

"GelBond Film," downloaded from http://www.bioproducts.com/product, Mar. 27, 2000, 3 pages.

Green J.A., et al., "Production of Polyclonal Antisera," Chapter 1, Immunochemical Protocols, Methods in Molecular Biology, The Humana Press, Inc., Totowa, NJ, 1992, vol. 10, pp. 1-6.

Green L.L., et al., "Antigen-Specific Human Monoclonal Antibodies From Mice Engineered With Human Ig Heavy and Light Chain YACs," Nature Genetics, May 1994, vol. 7, pp. 13-21.

Greg W., et al., "Humanized Antibodies," Immunology Today, Elsevier Science Publications, Ltd, UK, 1993, vol. 14 No. 6, pp. 243-246.

Greg W., et al., "Making Antibodies by Phage Display Technology," Annual Review of Immunology, 1994, vol. 12, pp. 433-455.

Gregoriadis G., "Liposome Technology: vol. 1 Preparation of Liposomes," CRC Press, NY, Table of Contents only, 1984, 7 Pages.

Harlow E.D., et al., "Sampling Serum," Chapter 5: Immunizations, Antibodies: A Laboratory Manual, 1988, pp. 116-120.

Henke C., "DNA-Chip Technologies Part 1: Research Fundamentals and Inudstry Catalysts," IVD Technology Magazine, Sep. 1998, 7 Pages.

Henke C., "DNA-Chip Technologies Part 2: State-of-The-Art and Competing Technologies," IVD Technology Magazine, Nov. 1998, 15 Pages.

Henke C., "DNA-Chip Technologies Part 3: What Does The Future Hold?," IVD Technology Magazine, 1998, 18 Pages.

Huse W.D., et al., "Generation of a Large Combinatorial Library of the Immunoglobulin Repertoire in Phage Lambda," Science, Dec. 8, 1989, vol. 246, pp. 1275-1281.

"Illustration of a Microtransponder for DNA-Probe Assays," Pharmaseq web page, Sep. 23, 2004, 1 page, Reetrieved from URL: http://www.pharmaseq.com/illustration.html.

(56) References Cited

OTHER PUBLICATIONS

Jellinek D., et al., "Potent 2'-Amino-2'-Deoxypyrimidine RNA Inhibitors of Basic Fibroblast Growth Factor," Biochemistry, American Chemical Society, 1995, vol. 34, No. 36, 14 Pages.
Jolly D., et al., "Viral Vector Systems For Gene Therapy," Review Article, Cancer Gene Therapy, Appleton & Lange, vol. 1, No. 1, 1994, pp. 1-64.
Kambil A., "Move Over Barcodes; Consumer-Goods Firms Eye Radio-Frequency ID," A Deloitte Research Engineering Technologies Brief, Deloitte Consulting, 2003, pp. 1-5.
Kohler., et al., "Continuous Cultures of Fused Cells Secreting Antibody of Predefined Specificity," Nature, Aug. 7, 1975, vol. 256, pp. 495-497.
Kuchinskas S., "IP Addresses for Coke Cans?," earthwebnews.com[online], Sep. 5, 2003, 3 Pages.
Lee Y., "Applications Note AN710, Antenna Circuit Design for RFID Applications," Microchip Technology, Inc, 2003, 50 pages.
Lonberg N., et al. "Antigen-specific Human Antibodies From Mice Comprising Four Distinct Genetic Modifications," Nature, Apr. 28, 1994, vol. 368, pp. 856-859.
Membrane Filters, Apr. 6, 2000, 10 pages, retrieved from http://www.voigtglobal.com/membfil.htm.
Michael S.I., et al., "Binding-Incompetent Adenovirus Facilitates Molecular Conjugate-mediated Gene Transfer by the Receptor-mediated Endocytosis Pathway," The Journal of Biological Chemistry, The American Society for Biochemistry and Molecular Biology, Incorporated, USA, Apr. 5, 1993, vol. 268, No. 10, pp. 6866-6869.
Moran E., et al., "Radio Frequency Tag Encoded Combinatorial Library Method for the Discovery of Tripeptide-Substituted Cinnamic Acid Inhibitors of the Protein Tyrosine Phosphatase PTP1B," Journal of the American Chemical Society, 1995, vol. 117, pp. 10787-10788.
Morishita R., et al., "Novel and Effective Gene Transfer Technique for Study of Vascular Renin Angiotensin System," Journal of Clinical Investigation, 1993, vol. 91, pp. 2580-2585.
"New RFID Tag with More Memory," Radio Frequency Identification Journal, Aug. 25, 2003, 2 Pages.
Office Action for Japanese Application No. 2007-540186, mailed on Mar. 2, 2011, 7 pages.
Pagratis N., et al., "Potent 2'-Amino-, and 2'-Fluoro-2'-Deoxyribonucleotide RNA Inhibitors of Keratinocyte Growth Factor," Nature Biotechnology, Jan. 1997, vol. 15, No. 1, pp. 68-73.
PCT/US01/40489, International Search Report, Jul. 6, 2001, 7 pages.
PCT/US2005/040500, International Preliminary Report on Patentability, Jul. 10, 2007, 7 pages.
PCT/US2005/040500, International Search Report, May 30, 2007, 3 pages.
PCT/US2005/040500, Written Opinion, May 30, 2007, 6 pages.
PCT/US2019/015920, International Search Report and Written Opinion, Mar. 20, 2019, 13 Pages.
"Polycarbonate Membrane Filters," Apr. 6, 2000, [Downloaded on Apr. 17, 2008], Downloaded from URL: http://www.2spi.com/catalog/spec.sub.--prep/filter3.html.
Rees A.R., et al., "Protein Engineering: A Practical Approach," Cold Springs Harbor Laboratory Press, 1993, pp. 1981-1982.
"Report: RFID Labels," Williams Inference Center, Longmeadow, MA, Sep. 28, 2000, vol. 27, No. 15, 4 pages.
Sambrook J., et al., "Ch: 16.30-16.60—Introduction of Recombinant Vectors into Mammalian Cells," Molecular Cloning, a Laboratory Manual, 2nd ed, Cold Spring Harbor Laboratory Press, Cold Spring Harbor, NY, 1989, pp. 16.30-16.60.
Service R.F., "Radio Tags Speed Compound Synthesis," Research News, Chemistry, Science, Oct. 27, 1995, vol. 27 p. 577.
Supplemental European Search Report for Application No. 01931132.3 mailed Aug. 14, 2008, 3 pages.
Tam R.C., et al., "Biological Availability and Nuclease Resistance Extend the in Vitro Activity of a Phosphoraothioate-3'hydroxypropylamine," Nucleic Acids Research, 1994, vol. 22, No. 6, pp. 977-986.
Taylor L.D., et al., "Human Immunoglobulin Transgenes Undergo and Class Rearrangement, Somatic Mutation and Class Switching in Mice That Lack Endogenous IgM," International Immunology, 1994, vol. 6, pp. 579-591.
"Technology," Vincogen, Jan. 29, 2004, 4 pages, retrieved from http://www.vincogen.com/technology.htm.
"The Write Stuff: Understanding the Value of Read/Write RFID Functionality," White Paper, Intermec, Technologies Corporation, USA, 2003, 6 pages.
Vincogen, "Investors Relationship," Vincogen Corporation, Jan. 28, 2004, 3 Pages, Retrieved from Internet: URL: http://www.vincogen.com/Investor/.htm.
Ward E.S., et al., "Binding Activities of a Repertoire of Single Immunoglobulin Variable Domains Secreted From *Escherichia coli*," Nature, Oct. 12, 1989, vol. 341, pp. 544-546.
Yun L., et al., "Modified RNA Sequence Pools for in Vitro Selection," Nucleic Acids Research, 1994, vol. 22, No. 24, pp. 5220-5234.
Zebra Technologies, "RFID: The Next Generation of AIDC," Application White Paper, Aug. 2004, pp. 1-13.
Zebra Technologies, "Zebra's RFID Readiness Guide: Complying with RFID Tagging Mandates," Application White Paper, Jan. 2004, pp. 1-9.

\* cited by examiner

INSTRUMENTS, DEVICES AND CONSUMABLES FOR USE IN A WORKFLOW OF A SMART MOLECULAR ANALYSIS SYSTEM

CROSS-REFERENCE TO RELATED APPLICATIONS

This application is a continuation of U.S. application Ser. No. 16/262,823, filed Jan. 30, 2019, which claims the benefit under 35 U.S.C. § 119(e) of U.S. Provisional Application No. 62/624,080, filed Jan. 30, 2018. The entire contents of the aforementioned applications are incorporated by reference herein.

BACKGROUND

Molecular analysis can be a time consuming and error-prone endeavor. Users may spend hours planning and defining their experiments, deciding which assays, reagents, instruments, and protocols they need to use. Additional barriers are presented by the need to ensure that reagents are functional (e.g., unexpired) and are utilized with the correct protocol. Various molecular analyses can be utilized to evaluate biomolecules. One type of analysis involves performing nucleic acid amplification and/or nucleic acid detection. One type of nucleic acid amplification involves a quantitative polymerase chain reaction (qPCR) to identify and quantify the presence of targets in a sample, typically in real time. These analyses utilize materials or items, also known as consumables, such as reaction plates and reagents, which interact in complex ways in the analysis workflow. In some cases a consumable is incorrectly stored and may have degraded, rendering it questionable for use in the analysis.

Molecular analysis typically involves many manual steps of liquid, reagent, and/or sample transfer onto particular reaction sites of a reaction substrate or reaction holder, such as a reaction chamber, channel, card, array, vessel, slide, or plate. Each step may require calculating and measuring the correct volume and/or concentration of liquid, reagent and/or sample to be used before transfer into the correct reaction site, which is typically, but not necessarily a defined region, location, or site located in or on the reaction substrate or reaction holder. Manual measuring and transferring to multiple reaction sites can increase the likelihood of analysis errors that may make results difficult to interpret. Additionally, scheduling the use of instruments used in the analysis may be challenging due to various users competing for the same instrument and/or management of an instrument from a remote location of one or more users.

A need therefore exists to facilitate tracking and usage of instruments and consumables used in molecular analysis and improve the overall ease, flexibility, and reliability of molecular analysis workflows.

BRIEF SUMMARY

The present invention is directed to a system for performing a molecular analysis. The molecular analysis can involve a workflow for a polymerase chain reaction (PCR). For example the workflow for the PCR molecular analysis may comprise a quantitative PCR (qPCR), an end point PCR (epPCR), a reverse transcription-PCR (RT-PCR), or a proximity ligation assay (PLA) involving PCR. The system, as disclosed herein, can comprise smart consumables. The smart consumables can include, for example, one or more smart reaction substrates or reaction holders (e.g., reaction plates or reaction arrays) and/or one or more smart a reagent containers The smart consumable may be a smart reaction holder, such as a reaction plate or a reaction array, and/or a smart reagent container. Each of the smart reaction substrates or reaction holders can comprise a reaction substrate or a reaction holder RFID tag. Likewise, each of the reagent containers can comprise a reagent container RFID tag. Working together or separately, the reaction substrate or reaction holder RFID tag(s) and the reagent container RFID tag(s) can store and share various data or information. The reaction substrate or reaction holder RFID tag(s) and the reagent container RFID tag(s) can both send and/or receive information. An RFID tag reader can read information stored on an RFID tag. An RFID writer can write (or rewrite) information to an RFID tag.

The reaction substrate or reaction holder can comprise at least one reaction site. Alternatively, the reaction substrate or reaction holder can comprise a plurality of reaction sites. One or more reaction sites of a reaction substrate or reaction holder can comprise a first reagent. In some cases, the first reagent of each reaction site of a reaction substrate or reaction holder is the same. In some other cases, the first reagent of each reaction site of a reaction substrate or reaction holder is different. Some portion (e.g., one or more) or all of the plurality of the reaction sites of a reaction substrate or reaction holder can comprise a first reagent. In some cases, some portion of the plurality of reaction sites may be left blank or empty. The first reagent of the reaction sites of a reaction substrate or reaction holder can be pre-spotted onto the reaction substrate or reaction holder. The first reagent can be dry-spotted onto the reaction substrate or reaction holder.

Where one or more reaction sites of a reaction substrate or a reaction holder comprises a first reagent, the reaction substrate or reaction holder RFID tag can comprise identifications of each reaction site and the corresponding first reagent contained by each reaction site. In some cases the first reagent comprises at least one primer and/or at least one probe. The at least one primer and/or the at least one probe in the first reagent of each reaction site can be the same or can be different. Accordingly, one or more reagent containers can comprises a second reagent, a third reagent, a forth reagent, etc. to be added to the first reagent of the reaction substrate or reaction holder. The reaction substrate or reaction holder RFID tag may encode or store data regarding characteristics of the first reagent and/or the reagent container RFID tag encoding data regarding characteristics of the second reagent. For example, the reaction substrate or reaction holder RFID tag can store an expiration date for the first reagent and/or the reagent container RFID tag can store an expiration date for the second reagent, third reagent, forth reagent, etc. comprised by the reagent container(s).

The reaction substrates or reaction holders and/or reagent containers of the system can also comprise a sensor for detection of changes in temperature, motion, light, and/or airflow, etc. The sensor can be coupled to the reaction substrate or reaction holder RFID tag and/or the reagent container RFID tag. Thus, the reaction plate RFID tag and/or the reagent container RFID tag, through coupling to one or more sensors, can each store a temperature history, a light exposure history, and/or a motion detection history for the reaction plate and/or the reagent container. In some cases, the RFID tags themselves may contain the one or more sensors. In other cases, the sensors are spatially separated from the RFID tags. The reaction substrate or reaction holder RFID tag and/or the reagent container RFID tag may also be comprise or be coupled to (directly or indirectly) a barcode.

The system can further include a smart instrument and/or a smart device. The smart instrument or smart device can comprise logic operable to provide a visual and/or verbal guide for a molecular analysis based on workflow information received from a reaction substrate or reaction holder RFID tag and/or a reagent container RFID tag. The instrument/device may comprise an RFID reader operable to read workflow information from the reaction plate RFID tag and/or the reagent container RFID tag. The instrument/device can comprise logic operable to access a network server system and/or a cloud to download the workflow for the molecular analysis. For example, the workflow may comprise an analysis protocol for the reaction substrate or reaction holder and/or reagent container. The analysis protocol can comprise an instruction for a liquid, reagent, or sample transfer to the reaction substrate or reaction holder. Likewise, the instrument/device can comprise an RFID writer and logic operable on the RFID writer to record a record on the reaction substrate or reaction holder RFID tag of a liquid, reagent, or sample transfer to the reaction substrate or reaction holder RFID tag. The record can comprise a reaction volume for the liquid, reagent, or sample transfer. Further, the instrument can comprise logic operable on the RFID writer to record a reaction site of the reaction substrate or reaction holder to which the liquid, reagent, or sample transfer is applied. The instrument may also comprise logic operable on the RFID writer to record a date and/or time at which the liquid, reagent, or sample transfer is applied to the reaction substrate or reaction holder, logic operable to apply the information stored by the reaction substrate or reaction holder RFID tag and/or the reagent container RFID tag to provide an instruction for mixing a first reagent on the reaction substrate or reaction holder with a second reagent stored by the reagent container, and/or logic operable to read the reaction plate RFID tag for an analysis protocol for the workflow. The instruction can comprise the reaction site on the reaction plate comprising the first reagent, and a transfer instruction for applying a liquid, another reagent, or sample to the reaction site and/or a reaction volume of the liquid, other reagent, or sample. The analysis protocol can comprise a liquid, reagent, or sample transfer instruction for applying reagents to the reaction substrate or reaction holder. The reaction substrate or reaction holder RFID tag can comprise an identification of a first reagent contained at a reaction site on the reaction substrate or reaction holder. The first reagent contained at the reaction site can comprise at least one primer pair and/or at least one probe. The reaction substrate or reaction holder RFID tag can comprise an identification of a next reaction substrate or reaction holder in the workflow for the molecular analysis.

Also provided herein are methods for performing a molecular analysis. The method may comprise steps for reading a reaction substrate or reaction holder RFID tag on a reaction substrate or reaction holder and/or reading a reagent container RFID tag on a reagent container, and applying information read from the reaction substrate or reaction holder RFID tag and/or the reagent container RFID tag to carry out a workflow for a molecular analysis. The methods can also comprise reading an identifications of a first reagent and a reaction site for the first reagent from the reaction substrate or reaction holder RFID tag; reading an identification of a second reagent from a reagent container RFID tag; reading from the reaction substrate or reaction holder RFID tag a temperature history for the reaction substrate or reaction holder, a light exposure history for the reaction substrate or reaction holder, and/or a motion detection history for the reaction substrate or reaction holder; reading from the reagent container RFID tag a temperature history for the reagent container, a light exposure history for the reagent container, and/or a motion detection history for the reagent container; reading from the reaction substrate or reaction holder RFID tag identifications of a plurality of reaction sites on the reaction substrate or reaction holder and a corresponding first reagent for each of the reaction sites; reading from the reagent container RFID tag an expiration date for a second reagent stored by the reagent container; reading from the reaction plate RFID tag data regarding characteristics of the reaction substrate or reaction holder, reading from the reagent container RFID tag data regarding characteristics of the second reagent; reading information for a workflow from the reaction substrate or reaction holder RFID tag and/or the reagent container RFID tag, and providing a visual and/or verbal guide for the workflow based on the information.

The methods may involve downloading a workflow for a molecular analysis from a network server system, the workflow comprising an analysis protocol for the reaction substrate or reaction holder. The analysis protocol can comprise an instruction for liquid reagent, and/or sample transfer of one or more reagents to the reaction substrate or reaction holder. The methods may involve operating an RFID writer to record a record on the reaction substrate or reaction holder RFID tag of a liquid, reagent, and/or sample transfer to the reaction substrate or reaction holder. The record may comprise a reaction volume of the liquid, reagent, or sample transfer.

The methods may involve operating the RFID writer to record an identification of a reaction site of the reaction substrate or reaction holder to which a liquid reagent, and/or sample transfer is applied; operating the RFID writer to record a date and/or time at which the liquid, reagent, and/or sample transfer is applied to the reaction substrate or reaction holder. The methods may involve applying information stored by a reaction substrate or reaction holder RFID tag and/or a reagent container RFID tag to provide an instruction for mixing a first reagent with a second reagent in the workflow for a molecular analysis. The instruction can comprise a reaction site on the reaction substrate or reaction holder comprising the first reagent, and an instruction for a liquid reagent, and/or sample transfer of the second reagent to the reaction site and/or a reaction volume of the second reagent.

The methods may include reading a reaction substrate or reaction holder RFID tag for an analysis protocol for the workflow. The analysis protocol can comprise, for example, an instruction for a liquid, reagent, or sample transfer of one or more reagents to the reaction substrate or reaction holder. In some methods, reading can be performed from a reaction substrate or reaction holder RFID tag and/or a reagent container RFID tag for an identification of a reagent contained at a reaction site on the reaction substrate or reaction holder; for an identification of at least one primer pair; for an identification of at least one probe; for an identification of a next reaction substrate or reaction holder and/or reagent container in the workflow for the molecular analysis. In some methods, writing can be performed to reaction substrate or reaction holder RFID tag and/or a reagent container RFID tag to write information about the reaction plate, the reagent container, the first reagent, the second reagent, and/or the molecular analysis to the and/or a reaction substrate or reaction holder RFID tag and/or a reagent container RFID tag.

Also provided herein are smart consumables for performing a molecular analysis workflow. The smart consumables can comprise at least one of: a reaction substrate or reaction holder comprising a reaction holder RFID tag, wherein the reaction holder RFID tag sends and receives and/or stores information regarding a workflow for the molecular analysis; and/or a reagent container comprising a reagent container RFID tag, wherein the reagent container RFID tag sends and receives and/or stores information regarding the workflow for the molecular analysis. A reaction substrate or reaction holder can comprise a plurality of reaction sites, wherein one or more reaction sites of the plurality comprises a first reagent, wherein the first reagent is the same or different at different reaction sites on the same a reaction substrate or reaction holder. The plurality of reaction sites can comprise at least 96 reaction sites, at least 384 reaction sites, at least 1536 reaction sites, at least 3072 reaction sites, or at least 12,288 reaction sites. The reaction substrate or reaction holder RFID tag can comprise identifications of each reaction site and the corresponding first reagent for each reaction site.

In some cases, the first reagent is dry-spotted (dried). In some cases, the first reagent is pre-spotted. "Pre-spotted," as used herein, refers to reaction substrates or reaction holders comprising a first reagent that has been added to the reaction substrate or reaction holder (or pre-loaded) by a manufacturer of the reaction substrate or reaction holder and is not directly added to the reaction substrate or reaction holder by the user. Pre-spotted reaction substrates or reaction holders can also be considered to be ready-to-use. "Ready-to-use," as used herein, can mean that only a limited number of additional reagents are needed to be added to the first reagent for a reaction to take place or can mean that only a liquid, such as water or a buffer, and/or a test sample may need to be added to the first reagent for a reaction to occur.

The reaction substrate or reaction holder RFID tag can store data regarding characteristics of the reaction substrate or reaction holder and/or the reagent container RFID tag can store data regarding characteristics of a reagent in the reagent container. The reaction substrate or reaction holder RFID tag and/or the reagent container RFID tag can store information to provide a visual or verbal guide for the workflow. The reaction substrate or reaction holder RFID tag can store a record of a reagent to be applied to the reaction substrate or reaction holder. The record can comprise a reaction volume of the reagent to be applied to the reaction substrate or reaction holder; an identification of the reaction site of the reaction substrate or reaction holder to which the reagent is applied, a date and/or time at which the reagent is applied to the reaction substrate or reaction holder; and/or an interaction of a first reagent with a second reagent in the workflow for the molecular analysis. The interaction can comprise a discrete reaction site on the reaction substrate or reaction holder comprising a first reagent, and an instruction for a transfer of a second reagent to the discrete reaction site. The instructions for a transfer of a second reagent can include instructions for a liquid transfer and may comprise a reaction volume of the second reagent. The reaction substrate or reaction holder RFID tag and/or the reagent container RFID tag can store an analysis protocol for a molecular analysis workflow. The analysis protocol can comprise an instruction for a liquid transfer of one or more reagents to the reaction substrate or reaction holder. The reaction substrate or reaction holder RFID tag can store an identification of a reagent contained at a reaction site on the reaction substrate or reaction holder. The reagent contained at the reaction site can comprise at least one primer pair and/or at least one probe. The reaction substrate or reaction holder RFID tag and/or the reagent container RFID tag can store an identification of a next reaction substrate or reaction holder and/or reagent container to be used in the workflow for the molecular analysis.

The reaction substrate or reaction holder may further comprise a temperature sensor, a light sensor, and/or a motion sensor coupled to the reaction substrate or reaction holder RFID tag, wherein the reaction substrate or reaction holder RFID tag stores a temperature history, a light exposure history, a motion detection history for the reaction substrate or reaction holder. The reagent container may further comprise a temperature sensor, a light sensor, and/or a motion sensor coupled to the reagent container RFID tag, wherein the reagent container RFID tag stores a temperature history, a light exposure history, a motion detection history for the reagent container. In some cases the reaction substrate or reaction holder and/or the reagent container further comprises a barcode. The temperature sensor, the light sensor, and/or the motion sensor can be directly or indirectly coupled to the reaction substrate or reaction holder RFID tag and/or the reagent container RFID tag.

Data regarding characteristics of the reaction substrate or reaction holder and/or the reagent container can comprise one or more of the following: an ID number; an expiration date; a part number; a barcode; a lot number; a part type; a storage temperature and/or storage temperature range; a reagent concentration; a recommended reagent concentration and/or volume to use in the workflow; a provision for liquid transfer support; a sales order number; a reagent name; an assay name; an assay location for a reagent to be used on the reaction holder; an assay ID; a suggested or required protocol for the molecular analysis; a sample name; a master mix name; an internet link or address (url); a reaction and/or a reagent volume; a test sample name; an analysis setting for the molecular analysis; a sample type; a molecular analysis type; and an instrument run protocol. Data regarding characteristics of the reaction substrate or reaction holder and/or the reagent container can be written and/or rewritten to the reaction substrate or reaction holder RFID tag and/or the reagent container RFID tag. The reaction substrate or reaction holder RFID tag and/or the reagent container RFID tag may have a capacity to store at least 8 kilobytes of information.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Figure 1:
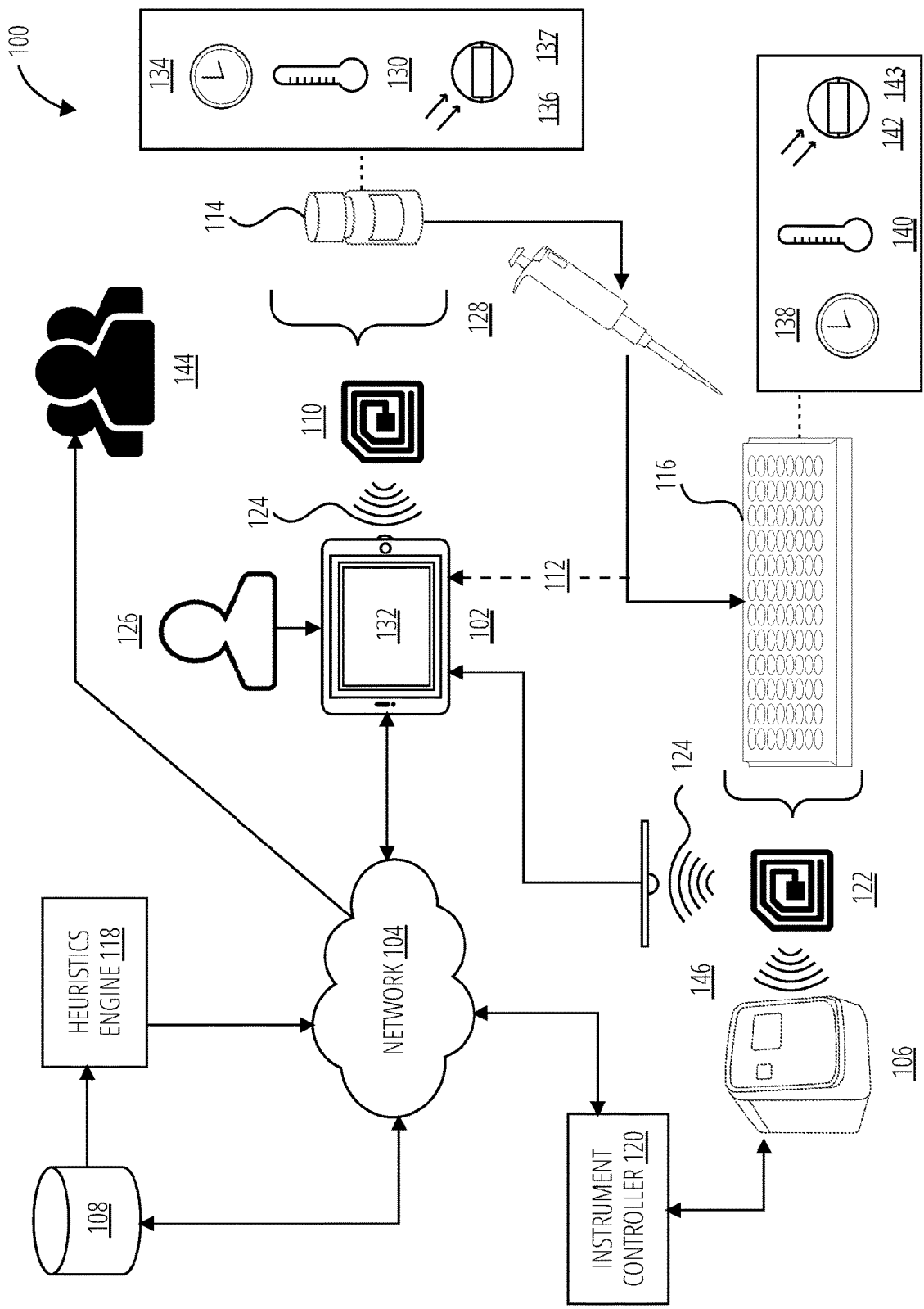
FIG. 1 illustrates a system diagram of system 100 in accordance with one embodiment.

Disclosed herein is a "smart" system that provides a connected workflow for performing a molecular analysis. In one embodiment, the molecular analysis is a polymerase chain reaction (PCR) workflow. In yet other embodiments, the molecular analysis is a real time or a quantitative PCR (qPCR), an end point PCR (epPCR), a proximity ligation assay (PLA) involving PCR, or a reverse transcriptase-PCR (RT-PCR) workflow. In some embodiments, the PCR is a singleplex PCR. In some other embodiments, the PCR is a multiplex PCR.

The smart system for molecular analysis as disclosed herein may be utilized according to various embodiments, including, but not limited to, the use of a smart instrument and various smart consumables. In some embodiments, the smart instrument is an instrument used for a polymerase chain reaction (PCR). In some embodiments, the smart consumables are reaction substrates or reaction holders and/or reaction reagents used for PCR. Thus, in some embodiments, the molecular analysis system, includes a smart PCR instrument, upon which embodiments of the present teachings may be implemented or used in conjunction with, including various smart consumables. In some embodiments, the PCR instrument, optionally, includes a heated cover that is placed over a plurality of reactions or samples contained in a smart reaction substrate or a reaction holder ("reaction substrate/holder"). In some embodiments, one or more reagents which are in conjunction with the smart instrument may be contained in one or more smart reagent containers. In some embodiments, one or more reagents which are placed onto or into a reaction substrate or reaction holder may be contained in one or more smart reagent containers.

As disclosed herein, the system includes one or more reaction substrates or one or more reaction holders, for example a reaction array, a reaction slide, or a reaction plate, which is "smart" or has Automatic Identification and Data Capture (AIDC) capabilities (is "AIDC-capable"). In some embodiments, the system also includes one or more "smart" reagent container(s) (e.g., a vessel, bottle, tube, vial, well, or chamber) with AIDC capabilities. In some embodiments, the system also includes one or more "smart" instruments or devices (e.g., a scanner, a display, or a thermocycler) with AIDC capabilities.

As used herein "smart" refers to an instrument, device, material or item, component, and/or part connected to other instruments, devices, materials or items, components and/or parts as part of a larger network and/or network cloud. Typically, a smart instrument, device, material or item, component, and/or part can be connected to other smart instruments, devices, materials or items, components, and/or parts through different wireless protocols or data transmissions such as, for example, Bluetooth, NFC, Wi-Fi, LiFi, 3G, etc., which can operate to some extent interactively and autonomously. As used herein, "network cloud," "cloud," or "the cloud" refers to a private, public or semi-public space that exists between the end points of a data transmission. In general, data that is transmitted enters the network cloud from one end point using a standard protocol and shares space in the network cloud with other data transmissions. Oftentimes, the data can also exit from the network cloud, where it may be encapsulated, translated and transported in myriad ways, in the same format as when it entered the network cloud.

In some embodiments the AIDC method used in either or both the smart reaction substrate/holder and/or the smart reagent container is a smart label. In some embodiments the AIDC method used in either or both the reaction substrate/holder and/or the reagent container is a Radio Frequency Identification (RFID) tag. Thus, in some embodiments, the system includes a reaction substrate/holder with a smart label or RFID tag, and/or a reagent container with a reagent container smart label or RFID tag. In some embodiments, when the system includes both a reaction substrate/holder, such as a reaction plate, with a reaction substrate/holder smart label or RFID tag, and one or more reagent container(s) with a reagent container smart label or RFID tag, the reaction substrate/holder smart label/RFID tag and the reagent container(s) smart label/RFID tag(s), together or collectively, can store and share information about the molecular analysis system. For example, system information can be stored or shared about samples, reagents, assays, users, and/or workflows used for particular molecular analyses, such as in a qPCR molecular analysis.

As used herein "RFID tag" or "tag" refers to a part, such as a chip, that stores digital data and/or information. In some embodiments, the tag comprises an integrated circuit and an antenna and a protective material that holds the pieces together and shields it from various environmental conditions. The protective material can depend on the application and RFID tags can come in a variety of shapes and sizes. The integrated circuitry may store data that can be communicated (e.g., sent or received) by a radio frequency transmitted by the antenna. The integrated circuit and antenna circuitry may be printed on the chip. An RFID tag can be read by an RFID reader using an antenna that emits radio frequencies to query the RFID tag. In some embodiments, the RFID tag is a "passive RFID tag" and does not have its own energy source, but responds to signals from a reader to transmit a signal. In other embodiments, the RFID tag is an "active RFID tag" and comprises its own power source, such as a battery. A "writable RFID tag" is an RFID tag that has memory space that can be written to by an RFID writer. "Smart labels" are similar to RFID tags and can incorporate both RFID and barcode technologies. In some embodiments, a smart label is made of an adhesive label embedded with an RFID tag, and may also include a barcode and/or other information. Some examples of RFID tags can be found in U.S. Pat. Nos. 6,147,662; 6,917,291; 5,949,049; 6,652,812; 6,112,152; and U.S. Patent Application No. 2003/0183683 all of which are herein incorporated by reference in their entireties for their disclosure of RFID tags, chips, labels, or devices, RFID readers, and RFID systems, their design and use.

In some embodiments, the reaction substrate or reaction holder, as disclosed herein, includes, but is not limited to a chamber, a channel, a card, an array, a vessel, a slide, or a plate. In various embodiments, the reaction substrate or reaction holder may be a reaction substrate/holder with a plurality of reaction sites. Some examples of a reaction substrate or a reaction holder with a plurality of reaction sites may include, but are not limited to, a multi-well plate, such as a standard microtiter 96-well, a 384-well plate, or a microcard, or a substantially planar support, such as a slide, and openarray, or an array. In some embodiments, the reaction substrate or reaction holder may be made of glass or plastic or any other suitable material evident to those of skill in the art. The reaction sites, in various embodiments of a reaction substrate or reaction holder, may include depressions, indentations, ridges, and combinations thereof, patterned in regular or irregular arrangements formed on the surface of the reaction substrate or a reaction holder.

In various embodiments, the one or more reagent containers, as disclosed herein, may include, but is not limited to a vessel, bottle, tube, vial, well, or chamber or any combination thereof. In some embodiments, the reagent container(s) may be made of glass or plastic or any other suitable material evident to those of skill in the art. The reagent container(s) may be of any size or dimension and may vary from one reagent container to the next, within the same system.

In some embodiments, the AIDC-capable reaction substrate or reaction holder, as disclosed herein, is a reaction plate or a reaction array. In some embodiments, the AIDC-capable reaction plate is an RFID-tagged plate or the AIDC-capable reaction array is an RFID-tagged array. In various embodiments, the reaction plate or reaction array will typically include a multiplicity of reaction sites, such as through holes or wells (e.g., a "multi-well reaction plate"). A multiplicity of reaction sites can include, for example, two or more reaction sites. For example, a reaction plate may have a multiplicity of 2, 10, 50, 100, 250, 500, 1000, 1500, or 3000, 10,000, 15,000 or more (or any number in between) reaction sites. In some preferred embodiments, a rectangular reaction plate or reaction array (e.g., in a 2×3 configuration) may have 6, 12, 24, 32, 48, 96, 384, 1536, 3072, or 12,288 reaction sites, although other configurations are contemplated by the present disclosure and will be evident to those of skill in the art. In some embodiments, the multi-well reaction plate is a 96-well plate or a 384-well plate. In some embodiments, the reaction plate is a polyethylene, polypropylene or a polycarbonate, multi-well plate. In some embodiments, the reaction plate is a MicroAmp™ plate or a MicroAmp™ Endura™ plate. In some embodiments, the reaction plate or reaction array is characterized by wells or holes with a volume capacity between 0.01 microliters (uL)/well or hole to 500 uL/well or hole. In some embodiments, the well or hole volume capacity can be 0.01 ul or more. In some embodiments, the well or hole volume capacity is between 0.5 uL to 1 milliliter (mL). In some embodiments, the size of a well or hole is characterized as having a reaction volume of 0.001 mL, 0.02 ml, 0.03 mL, 0.1 mL or 0.2 mL.

In some embodiments, some portion of or all of the reaction sites of a reaction substrate or reaction holder, such as a multi-well reaction plate, may contain a first reagent. In some embodiments, the reaction plate is pre-spotted (and, optionally, made ready-to-use) with a first reagent. The first reagent at each reaction site or well that contains the first reagent may be the same, or the first reagent may (and often will) vary across the different reaction sites. Herein "first reagent" means one or more reagents, such as on the reaction plate, which may be the same reagent or different reagents from one reaction site to the next. In some embodiments, the first reagent includes a single reagent, for example, a sample, a buffer, a primer, a probe, an enzyme, or dideoxynucleotides (dNTPs) for use in a molecular analysis, such as qPCR. In some other embodiments, the first reagent may include any combination of reagents selected from, but not limited to, for example a sample, a buffer, a primer, a probe, an enzyme, and/or dNTPs. In some embodiments, the first reagent can include a combination of reagents that may constitute a master mix or storage mix, for use in a molecular analysis, such as qPCR. Thus, in some embodiments, the first reagent at one reaction site may be a combination of reagents which is the same or is a different combination of reagents as the first reagent at another reaction site within the same multi-well plate.

In some embodiments of the disclosed system, there may also be one or more AIDC-capable reagent container(s), used in addition to or separate from the AIDC-capable reaction substrate or reaction holder (e.g., a reaction plate). In some embodiments, the reagent container may be used in place of or alternative to a reaction plate. In some embodiments, the reagent container may be used in combination with a reaction plate. In some embodiments where a reagent container is used without a reaction plate, the reagent container(s) holds a first reagent, a second reagent, a third reagent, and so on. In some embodiments where a reaction container is used in addition to a reaction plate which contains a first reagent, the reagent container(s) may hold a second reagent, a third reagent, and so on. In some other embodiments, the second, third, forth, etc. reagent is added to at least one of the reaction sites of the reaction plate at one or more particular points in the molecular analysis, e.g., at one or more particular points in the qPCR workflow. Herein, "second reagent", "third reagent", "forth reagent", etc. refers to any reagent added to a first reagent, such as a first reagent on a reaction plate or a first reagent in another reagent container, as part of the analysis, not necessarily in any particular order, and each of the "first reagent", "second reagent", "third reagent", "forth reagent", etc. may include the same or different reagents in each of the different reagent containers. In some embodiments, the first, second, third, forth, etc. reagent may each include a single reagent or a mixture of different reagents, such as in a master mix or a storage mix.

As disclosed above, either or both of the reaction substrate or reaction holder and/or the reagent container(s) may be coupled to an Automatic Identification and Data Capture (AIDC) technology, such as radio-frequency identification (RFID), and may include a smart label and/or an RFID tag. In general, "RFID technology" or "RFID" refers to a technology whereby digital data and/or information encoded in RFID tags or smart labels are captured by a reader via radio waves. RFID is similar to barcoding in that data from a tag or label can be captured by a device that reads the data and/or information. RFID, however, has several advantages over systems that use barcode asset tracking software. One of the most notable is that RFID data/information can be read outside the line-of-sight, whereas barcodes must typically be at least partially aligned with an optical scanner.

In some embodiments, the RFID tags or smart labels as disclosed herein, can both send and receive information. In some embodiments, such information can be stored on the RFID tag or smart label for subsequent usage or recall. In some embodiments, information can be written to (or rewritten to) the RFID tag or smart label. In some embodiments of the disclosed system, the RFID tags or smart labels may have a capacity to hold 2 kilobytes (kB) or more of information. In some embodiments, the RFID tags or smart labels have a capacity of at least 2 kilobytes, 3 kilobytes, 4 kilobytes, 5 kilobytes, 6 kilobytes, 7 kilobytes, 8 kilobytes, 10 kilobytes, 12 kilobytes, 16 kilobytes, 32 kilobytes, 64 kilobytes, 128 kilobytes, 256 kilobytes, 512 kilobytes (or any number in between). In some embodiments, the RFID tags or smart labels have a capacity to hold at least 8 kilobytes of information. In some other embodiments, the RFID tags or smart labels have a capacity to hold between 4 to 512 kilobytes of information. In some other embodiments, the RFID tags or smart labels have a capacity to hold between 8 to 64 kilobytes of information.

In some additional embodiments, the reaction substrate or reaction holder and/or the reagent container(s) as disclosed herein may further include a temperature sensor, a light sensor, and/or a motion sensor coupled to the reaction substrate or reaction holder and/or reagent container(s). In some embodiments, the temperature sensor, light sensor, and/or motion sensor may be part of a smart label or an RFID tag, for example, wherein the reaction substrate or reaction holder RFID tag and/or the reagent container RFID tag reads and stores a temperature history, light history, and/or motion history for the reaction substrate or reaction holder and/or the reagent container obtained from the temperature sensor, light sensor, and/or motion sensor coupled to the reaction substrate or reaction holder and/or reagent container. In some embodiments a temperature sensor coupled to the reaction substrate or reaction holder and/or reagent container, either as a separate piece or as part of an RFID tag on the reaction substrate or reaction holder and/or reagent container, senses or stores a temperature exposure history for the reaction substrate or reaction holder and/or reagent container. In some embodiments a light sensor coupled to the reaction substrate or reaction holder and/or reagent container, either as a separate piece or as part of an RFID tag, senses or stores a light exposure history for the reaction substrate or reaction holder and/or reagent container. In some embodiments a motion sensor coupled to the reaction substrate or reaction holder and/or reagent container, either as a separate piece or as part of an RFID tag on the reaction substrate or reaction holder and/or reagent container, senses or stores a motion or shock exposure history for the reaction substrate or reaction holder and/or reagent container.

In some embodiments, each reaction site of the reaction substrate or reaction holder may include a first reagent which is deposited onto the reaction substrate/holder, and the reaction substrate/holder RFID tag may include identifications of each reaction site on the reaction substrate/holder and a corresponding reagent, sample, or assay contained by each reaction site. The reagent deposited at each reaction site may include at least one assay comprising at least one primer and at least one probe. In some embodiments, the reagent is dry-spotted (i.e., dried) onto the reaction sites of the reaction substrate/holder. In some embodiments, the reagent is lyophilized. The reaction substrate or reaction holder RFID tag and/or the reagent container(s) RFID tag(s) may also store an expiration date for the first, second, third, etc. reagent(s) placed or stored in or on the reaction substrate or reaction holder and/or the reagent container(s), as well as any other information about the reagent(s), the workflow, and/or the analysis, as detailed below. For instance, in some embodiments, a reaction substrate or reaction holder RFID tag, such as a reaction plate RFID tag, may contain information including, but not limited to, the plate layout defining which assay(s) are contained in each well; the recommended protocol to be run for a given assay or analysis; the recommended dye set to be run for a given assay or analysis; the bar code of the plate; urls (links to World Wide Web pages; www sites), to a Material Safety Data Sheet (MSDS), a Certificate of Analysis (COA), protocol(s), and other relevant literature; and/or a unique ID that can be used for purposes such as reordering or tracking usage. In some embodiments, the RFID tag or smart label may also comprise some security information to encrypt experimental data as a means to support items that a customer may deem sensitive and/or to provide counterfeit countermeasures, including manufacture-specific, lab-specific, and/or user-specific information or digital security locks.

In some embodiments, the reaction substrate or reaction holder (e.g., a reaction plate) RFID tag may encode data regarding characteristics of a first reagent, and the reagent container RFID tag may encode data regarding characteristics of a second reagent. These characteristics may include, for example: assay information for the molecular analysis, expiration dates for the various reagents involved in the molecular analysis, storage conditions (including temperature storage, light exposure, motion/shock detection history) for the reaction substrate or reaction holder and/or reagent container, part /lot/catalog numbers for the reaction substrate or reaction holder or the various reagents, detailed information about what assays, samples, or reagents were dispensed into which reaction sites of the reaction substrate or reaction holder, and usage rate or used volumes of the reagents applied to the reaction substrate(s) or reaction holder(s) or contained by the reagent containers (e.g., based on the volume used per reaction or at each reaction site).

In some embodiments, an instrument that includes a smart label or RFID tag reader (i.e., is smart enabled) is used to read workflow information from the reaction substrate or reaction holder smart label or RFID tag and/or the reagent container(s) smart label(s) or RFID tag(s), and to provide a visual and/or a verbal guide for the workflow based on the workflow information received from the label or tag. The smart-enabled instrument may access a network server system to download the workflow for the molecular analysis, including an analysis protocol for the reaction substrate or reaction holder and/or reagent container and other useful information, for example, for carrying out an experimental protocol or data analysis. In some embodiments the protocol may include instructions for a liquid reagent, or sample transfer to the reaction substrate or reaction holder. In some embodiments the instructions are for transfer of a second reagent, such as from a reagent container, to the reaction sites of the reaction substrate or reaction holder that contains or is pre-loaded with a first reagent. In some other embodiments the instructions are for liquid transfer of a second, third, forth, etc. reagent, such as from one or more reagent container(s), to a first, second, third, forth, etc. reagent of another reagent container. In some cases, the instrument may read the reaction substrate or reaction holder or reagent container smart label or RFID tag, directly, to obtain information, such as the analysis protocol for the workflow, instead of accessing a network server system for the information.

In some embodiments, the information stored on the smart labels or RFID tags include information or attributes about the reaction substrate or reaction holder and/or the reagent(s) themselves. Such information can include, for example, an ID number, a part number, a lot number, a vendor name and/or location, a part type (e.g., 96-well plate or 384-well plate; 96-well 0.1 mL reaction volume plate or 96-well 0.2 mL reaction volume plate; etc.), a storage temperature such as a recommended temperature range, and/or a sales order number. Any of this information may also or alternatively be downloaded from a network based on a reaction substrate or reaction holder ID or reagent ID read from the smart label or RFID tag on the reaction substrate or reaction holder and/or reagent container.

In some embodiments, the information stored by the smart labels or RFID tags may go beyond characteristics of the reaction substrate or reaction holder and/or the reagents, and may include information such as run protocols, analysis instrument settings, identifications of who planned the experiment and prepared the physical reaction or assay, assay type, (e.g., gene expression, microRNA, etc.), which types of instruments the reaction substrate or reaction holder was run on, next step(s) in the analysis workflow (examples qPCR-CE instrument etc.), who ran the reaction substrate or reaction holder and using which instrument(s), and possible causes of error in the experiment. Any of this information may also or alternatively be downloaded from a network based on a reaction substrate or reaction holder ID or reagent ID read from a smart label or RFID tag on the reaction substrate or reaction holder and/or reagent container(s).

Additional data that may be stored by the smart labels or RFID tags include analysis objectives and hypotheses, analysis methodology, results and conclusions, identification of analysis materials such as pipettes and protocols for their use, replicates and controls used, templates to use for a given assay, product recommendations based on new releases/enhancements to the chemistry the user is running or alternate products which can yield better run quality based on what is observed from post run quality metrics published by utilized instruments, related publications, active studies, and research trials, community networks interested in the same study, and trend analysis. Any of this information may also or alternatively be downloaded from a network based on a reaction substrate or reaction holder ID or reagent ID read from the smart label or RFID tag on the reaction substrate or reaction holder and/or reagent container(s).

Herein, the term "lab bench assistant" or "lab assistant" refers to an instrument or a device that includes logic to read smart labels and/or RFID tags of the reaction substrate or reaction holder and/or the reagent container(s) using a smart label or RFID reader. In some embodiments, the lab assistant is able to visually display and/or verbally communicate information stored on the smart labels or RFID tags (or provide such information to an external device such as a computer system, for display or verbal communication). In some embodiments, the lab assistant can write information thereto using a smart label or RFID writer, to facilitate and improve the workflow for molecular analysis. In some embodiments, the lab assistant may also or alternatively download information from a network and/or send information to a network for storage or retrieval from another part or device on the network.

Therefore, as noted, a lab bench assistant may include a smart label or RFID writer and may write (record) information on a reaction substrate or reaction holder smart label or RFID tag and/or a reagent container(s) smart label or RFID tag including any of the information noted above and further described herein. For example, one or more liquid, reagent, or sample transfers to the reaction substrate or reaction holder and/or the reagent container may be recorded, where the record can include information such as a reaction volume of the liquid, reagent or sample transfer, the reaction site on the reaction substrate or reaction holder and/or the reagent container to which the liquid, reagent, or sample transfer is applied, a date and/or time at which the liquid, reagent, or sample transfer is applied to the reaction substrate or reaction holder and/or the reagent container and/or by whom.

In some embodiments, the lab assistant may apply the information stored by the reaction substrate or reaction holder smart label or RFID tag and the reagent container smart label or RFID tag to provide instructions for mixing the first reagent on the reaction substrate or reaction holder with the second reagent stored by the reagent container(s). The instructions may include identifying the reaction site on the reaction substrate or reaction holder where the first reagent is deposited, and transfer instructions for applying the second reagent to the reaction site, and/or a reaction volume of the second reagent to apply.

Thus, the reaction substrate or reaction holder, like the reagent container, may be "smart". In complicated molecular analyses involving multiple reaction substrates or reaction holders, one or more of the reaction substrate or reaction holder smart labels or RFID tags may include an identification of a next reaction substrate or reaction holder in the workflow, thus forming a chain or sequence of reaction substrate or reaction holder and/or reagent containers to use in the molecular analysis.

Like the reagent container, the reaction substrate or reaction holder may include a temperature sensor (either in combination with other sensors or by itself) coupled to the reaction substrate or reaction holder RFID tag, with the reaction substrate or reaction holder RFID tag reading the temperature sensor and storing a temperature history for the reaction substrate or reaction holder. The reaction substrate or reaction holder may also include a light sensor (either in combination with other sensors or by itself) coupled to the reaction substrate or reaction holder RFID tag, with the reaction substrate or reaction holder RFID tag reading the light sensor and storing a light exposure history for the reaction substrate or reaction holder. The reaction substrate or reaction holder may also include a motion sensor (either in combination with other sensors or by itself) coupled to the reaction substrate or reaction holder RFID tag, with the reaction substrate or reaction holder RFID tag reading the motion sensor and storing a motion or shock exposure history for the reaction substrate or reaction holder. In some embodiments, the temperature sensor, light sensor, and/or motion sensor may be a separate component located on the reaction substrate or reaction holder or they may be part of the RFID tag component itself.

At various points in the molecular analysis workflow, the system may provide notifications to the user that are based on stored smart label or RFID information. The notifications may for example suggest that it's time to reorder certain consumables such as reagents added to a reaction plate, and may suggest particular product codes or other indications of which reagents to order. Notifications and other information to facilitate the molecular analysis workflow may be delivered in a conversational interface from the lab instrument, for example using a chatbot or voice application. Machine learning may be utilized to improve and update the information for various analyses and subsequently stored on a smart label, RFID tag, and/or in a network cloud system.

In one embodiment, referencing FIG. 1, a molecular analysis system 100 optionally includes any one or more, in any combination and any order, of the following components: display device 102, a network 104, a controlled memory data structure 108, a heuristics engine 118, a reaction plate 116, a reagent container 114, a liquid transfer device 128, an instrument 106, and an instrument controller 120. Additional consumables and instruments may of course be utilized, but for purposes of concise illustration, the set in FIG. 1 has been limited as shown. In some embodiments, the molecular analysis system, includes an instrument, a reaction plate and/or a reagent container. In some embodiments, the molecular analysis system, includes an instrument, an instrument controller, a reaction plate and/or a reagent container. In some embodiments, the molecular analysis system, includes an instrument, an instrument controller, a reaction plate and/or a reagent container, and a display device.

In some embodiments, the display device 102 displays a user interface 132 to a user 126 that communicates information to the user about, for example, the consumables, assays, and protocols utilized in an experiment. The display device 102 may include an RFID reader 124 that reads information stored in a reagent container RFID tag 110 and/or a reaction plate RFID tag 122. After scanning the reagent container RFID tag 110, the display device 102 may display information about the reagent in the reagent container 114 such as the name, properties, product information, and storage or sensor history information, as well as any of the other information described herein. The display device 102 may also communicate the scanned information from the reagent container RFID tag 110 through a network 104 to retrieve protocol instructions for using the reagent. In some particular embodiments, this and other information for the molecular analysis is stored in a controlled memory data structure 108.

After reading the reaction plate RFID tag 122, the display device 102 may display information about the reaction plate 116 such as the name of the plate, properties, assay information, reaction site template information, production information, and storage or sensor history 138, as well as any of the other information described herein. The storage information for the reaction plate 116 may be collected through the use of a temperature sensor 140, a light sensor 142, and/or a motion sensor 143 and may be stored as sensor history information 138 that includes the light exposure history, temperature history, motion history, and/or possibly other history information as well (e.g., exposure to air). The display device 102 may also communicate the information scanned from the reaction plate RFID tag 122 through a network 104 to retrieve protocol information, assay information, or any other information as disclosed herein. The display device 102 may also communicate the collective information scanned from the reaction plate RFID tag 122 and the information scanned from the reagent container RFID tag 110, through a network 104 to retrieve protocol information, assay information, or any other information as disclosed herein.

The display device 102 may also receive information from a heuristics engine 118 regarding improvements or suggestions based on scientific literature and past experiments utilizing the scanned reagent and plate combination. This information may be obtained from the network 104 or from any one or more of the RFID tags used in the system. The heuristics engine 118 may learn from analysis results to improve future suggestions.

The reaction plate 116, for example a microtiter plate, may include 6, 12, 24, 48, 96, 384 or 1536 sample wells or through holes arranged in a 2:3 rectangular matrix of reaction sites. Each reaction site can serve as a vessel for performing a molecular reaction. During an analysis, each site may include any combination of reagents and/or a test sample used to perform the molecular reaction as well as the use of a laboratory instrument to control the kinematics of the reaction and measure the resulting reaction products.

In some embodiments, the reaction plate 116 includes a reaction plate RFID tag 122 utilized by the instrument to read, in various embodiments, any of the information described herein. In some embodiments this information includes a history 138 for the reaction plate, such as for example temperature history, light exposure history, and/or motion detection history. The reaction plate 116 may be configured as a pre-spotted plate containing a plurality of "assays" (e.g., primers and probes), each assigned to specific sites of the reaction plate. In some embodiments, scanning the reaction plate RFID tag 122 may provide a user with a layout of the assays within the sites. A user may also scan the reagent container RFID tag 110 of the of a reagent container 114 for information about reagents to add to the reaction sites of the reaction plate 116.

In some embodiments, the probes, as disclosed herein are a hydrolysis probe which exploits the 5' exonuclease activity of certain DNA polymerases, such as Taq, to cleave a labeled probe during PCR. One specific example of a hydrolysis probe is a TaqMan probe. In one embodiment, the disclosed probes are hydrolysis probes that further contains a reporter dye at the 5'-end of the probe and a quencher dye at the 3'-end of the probe. During a PCR, cleavage of the probe separates the reporter dye and the quencher dye, resulting in increased fluorescence of the reporter. Accumulation of PCR products can then be detected directly by monitoring the increase in fluorescence of the reporter dye. When the probe is intact, the close proximity of the reporter dye to the quencher dye results in suppression of the reporter fluorescence primarily by Forster-type energy transfer (Forster, 1948; Lakowicz, 1983). During PCR, if the target of interest is present, the probe specifically anneals between the forward and reverse primer sites. The 5' to 3' nucleolytic activity of a Taq DNA polymerase, for example, then cleaves the probe between the reporter and the quencher only if the probe hybridizes to the target. Such probes are referred to as "TaqMan" probes. In some embodiments of the probes, as disclosed herein, the 3' end of the probe is blocked to prevent extension of the probe during PCR. Examples of such hydrolysis probes can be found in Holland and Gelfand (1991) Proc. Natl. Acad. Sci. USA 88:7376-80; Heid et al. (1996) Genome Methods 6:986-94; U.S. Pat. Nos. 7,205, 105; 6,927,024; and 5,210,015, each of which is herein incorporated by reference in its entirety for its disclosure of 5' exonuclease or hydrolysis probes, their design, and use.

In some additional embodiments, the system can include single or multiple (e.g., 2, 3, 4, or more) built-in antennas and/or RFID writers and/or RFID readers. In some embodiments, multiple built-in antennas and/or RFID writers and/or RFID readers are spatially separated. In some embodiments, for example, multiple built-in antennas and/or RFID writers and/or RFID readers are located in opposite locations to one another. In some embodiments, the system comprises two built-in (e.g., left-side and right-side) antennas and/or two (e.g., left-side and right-side) RFID readers each of which may be enabled to read the RFID tag information of an RFID tag attached to a reaction plate. In some embodiments, the multiple antennas and/or the multiple RFID readers are used to pre-check the correct orientation of a reaction substrate or reaction holder in the instrument and/or to ensure the user is running the correct assay or protocol for a given reaction plate, for example. In some embodiments, reaction plate orientation is determined based upon which of the multiple antennas and/or RFID readers receives a signal from the reaction plate RFID tag. In some embodiments, after a run, the one or more RFID writers can write information onto the RFID tag to mark the reaction plate as "used" which can prevent the reaction of the reaction plate from being re-run or repeated. In some embodiments, the information can also be transmitted to a remote location, e.g. for inventory control and procurement purposes. In some embodiments, the two or more RFID tag readers also allow detection of the orientation of the reaction plate. If a user does not place the reaction plate in an expected or typical orientation, for example, system software can account for the error for display and analysis purposes and reset the template information and labels accordingly and/or notify the user of the skewed orientation. For example, if a user places a reaction plate into the instrument in a direction that is 180 degrees off from the direction it is meant to be placed, the RFID readers can detect the placement and orientation of the plate and notify the user of possible error. The user can also be provided an option to rewrite, in reverse direction, the location of various labels and/or the layout template for each of the wells, used for tracking multiple reaction sites, for example.

In some embodiments, a reagent container 114 optionally stores a reagent identifiable by a reagent container RFID tag 110. The reagent container RFID tag 110 can be utilized to communicate various information, including, but not limited to, specific information about the reagent (e.g., name, concentration, handling instructions, available stock, etc.), the reagent's production, (e.g., lot number, production date, etc.) and storage information (e.g., storage temperature, light exposure history, motion history, etc.) to an RFID reader. The storage information for the reagent container 114 may be collected through the use of a temperature sensor 130, a light sensor 136, and/or a motion sensor 137 and may be stored as sensor history information 134 that includes the light exposure history, temperature history, motion history, and/or possibly other history information as well (e.g., exposure to air). In some embodiments, an RFID writer may write this information onto a reagent container RFID tag 110 to be read by an RFID reader 124. After the reagent container RFID tag 110 is scanned by an RFID reader 124, the display device 102 may display or communicate information for the specific reagents, reactions, or assays as read from the RFID tag 110.

In some embodiments, after the reagent container RFID tag 110 and/or the reaction plate RFID tag 122 have been scanned, the display device 102 may retrieve protocol information regarding the specific volumes of a reagent that need to be transferred into each well of a reaction plate. The protocol information may be retrieved from the stored information in a controlled memory data structure 108 communicated to the display device 102 through a network 104, or from the reaction plate 116 and/or reagent containers 114 themselves. The protocol information may be used to configure a liquid transfer device 128 (e.g., El-ClipTip™ Bluetooth™ Electronic Single or Multi-Channel Pipettes) for transferring the reagent into the wells of the reaction plate 116. The protocol information may also be utilized to inform the user which reaction sites a reagent or sample should be transferred to.

The reagent stored within the reagent container 114 may be transferred to a reaction plate 116 through the use of a liquid transfer device 128. The liquid transfer device 128 may be a pipette (e.g., El-ClipTip™ Bluetooth™ Electronic Single or Multi-Channel Pipettes). The liquid transfer device 128 may be configured to deliver a calculated volume of a reagent into a predetermined reaction site of the reaction plate 116 according to the protocol for the experiment/investigation displayed through the display device 102. After the liquid transfer has occurred, the display device 102 may receive indication from the user that the reaction plate 116 is ready to be run on an instrument (e.g., for PCR). The indication provided by the user may signal the display device 102 to communicate the details to the controlled memory data structure 108 to be stored for the specific reaction plate RFID tag 122. In some configurations, the user may input liquid transfer information 112 about the reaction sites where the reagent was added, as well as any notes regarding the liquid transfer process. In some embodiments, the RFID tag on the reaction plate may be read by one or more RFID tag readers and/or one or more antennas to determine if the orientation of the plate is correct or needs adjusting. In some embodiments, a first RFID tag reader and a second RFID tag reader may search for a signal from the RFID tag on the reaction plate. Depending on which RFID tag reader receives a signal (or, for example, receives the stronger of the signals received by multiple RFID readers), then the orientation of the reaction plate can be determined and, if necessary, reaction site information can be rewritten to the RFID tag and/or a signal sent to the user to indicate that the reaction plate has been incorrectly placed (i.e., 180 degrees facing the wrong way in a horizontal position).

In some embodiments, after one or more reagents have been added to the reaction plate 116, the user 126 may schedule a time on an instrument 106 to start their experiment. In some configurations, the analysis may involve a quantitative polymerase chain reaction (qPCR). The user may utilize an RFID reader 146 contained within the instrument 106 to scan the reaction plate RFID tag 122, and to communicate/receive information for the specific reaction plate RFID tag 122 either from the tag itself or by way of the network 104. The instrument 106 may utilize the reaction plate RFID tag 122 information to set operation parameters. The user may utilize a scheduling tool displayed in the user interface 132 of the display device 102 to set up a time to run the reaction plate 116 on the instrument as well as the specific parameters (e.g., duration, temperature) to run the analysis on the instrument. In some embodiments, after the instrument 106 has been scheduled to run the reaction plate 116, an instrument controller 120 can be configured with the instructions to operate the instrument 106. For example, when the scheduled time is detected, the instrument controller 120 begins the experiment on the reaction plate 116. The instrument controller 120 may then detect results for the analysis and communicate the information to the user across the network 104, and/or write them to the reaction plate RFID tag 122. In some embodiments, the results of the analysis may be later analyzed by the heuristics engine 118. In some other embodiments, information stored on a controlled memory data structure 108 may be communicated to a user group 144 for the purpose of collaboration on the analysis and/or to check on the progress/resource utilization by users within a lab.

In some embodiments, the user may access digital information (see above for examples) associated with their analysis materials like pre-spotted plates, reagents etc., from a lab bench assistant (a digital touch point located in the wet lab or, for example, a computer system).

The lab bench assistant may track the time capsule/historical information linked to the analysis regarding who planned the analysis and prepared the physical plate, what reagents, buffers, assays etc., were used for the analysis, detailed information about what assays, reagents, and samples were utilized in which reaction sites, which types of instruments the plate was run on and next step(s) in their workflow (examples qPCR-CE instrument etc.). Other information available at the lab bench assistant includes who ran the plate on which instrument and tracking the causes of error by reviewing all related information used in the analysis. This information when the information is written back to the plate 116 by the lab bench assistant for traceability, or may be written or recorded to a network server and/or other storage medium.

The lab bench assistant may provide the user with notifications for any reagents/assays that are on a recall list, or which require reorder or replacement with improved products. User notifications may be delivered automatically to all the instances of lab bench assistant which have scanned a reagent on the recall list or at the time of scanning if not available in the reagent history.

The lab bench assistant may provide notifications for reagents which are about to expire and which have already expired. The error rate may be reduced so that any expired reagent is prevented from being added to a plate. The lab bench assistant may allow users to re-order reagents/assays/plates easily as all the information like order number, lot number, part number, etc. is easily available and can be recorded and retained by the system.

The lab bench assistant may track usage rate of the reagents, based on the volume used per reaction site across all the plates ran in the lab, and by doing so may notify the user in advance that they are about to run out of a reagent. In some cases, the lab bench assistant may automatically order the reagent for the user(s).

The lab bench assistant may come with machine learning capabilities to reduce reagent waste. Based on user's inventory and usage, the lab bench assistant may be able to predict when certain consumables may expire. The lab bench assistant may be able to provide users with altered run plans to best optimize usage of reagents at hand. This could also extend beyond the current user and look at inventories used by users from same organization (location based) and then optimize reagent use and reduce waste for a lab to an organization.

When providing an altered run plan, the lab bench assistant may identify altered run plans not just from the plate layout, but also based on which is the best instrument type to perform the specific run protocol.

The lab bench assistant may provide a workflow to calculate reaction volume of samples, reagents, buffer, and etc., based on the required concentration and reaction volume/reaction site. Once the volume is calculated per reaction, samples and reagents can be assigned to particular reaction sites, and electronic protocols provided for use with various consumables, as disclosed herein, as well as liquid transfer devices, as disclosed herein, such as an El-ClipTip™ Bluetooth™ Electronic Pipette.

The lab bench assistant may also guide the user in the liquid dispensing step to avoid any errors. The guidance could be enabled by conversational interface (like chatbots/voice).

The lab bench assistant may enable smart instruments to automatically create run files. When a "smart" reaction plate is created it may include in its RFID tag the information or links to information for reagents, protocols, and assay information for the reaction plate. As the reaction plate travels to each downstream instrument, each instrument may record its use of this reaction plate and whenever applicable use the information from the reaction plate to automatically perform the instrument run protocol.

Any information received by and/or sent from the lab bench assistant, as described above, may also be received by and/or sent from an instrument 106, and an instrument controller 120. In some embodiments, an instrument 106, and/or an instrument controller 120 and/or a lab assistant, collectively share information obtained from a reaction plate RFID tag and/or a reagent container RFID tag. Having a mobile lab assistant allows a user to be in a separate location from an instrument 106, and/or an instrument controller 120 and still be notified of received from the reaction plate and/or the reagent container RFID tag. Cross-communication among an instrument 106, and/or an instrument controller 120 and/or a lab assistant also allows the user to remotely communicate with the an instrument 106, and/or an instrument controller 120 using the lab assistant, for example, to send user requests or information directly to the instrument 106, and/or an instrument controller 120 pertaining to the instrument run protocol.

After the instrument run protocol, the user may generate publication-ready templates that contain data packets used for instrument run protocol and analysis. The data packet may be reused by any scientist from within or outside the organization to recreate the analysis. The data packet may include analytical objectives/hypothesis, materials and methods, results/conclusion, run protocols, electronic liquid transfer (e.g., El-ClipTip™ Bluetooth™ Electronic Pipette) protocols, part numbers of products used, number of replicates and controls used, etc.

The lab bench assistant may have capabilities to provide users with product recommendations based on new releases/enhancements to the chemistry the user is running or alternate products which may yield better run quality based on what is observed from post run quality metrics published by smart instruments.

The lab bench assistant may have capabilities to provide users with related publications, active study and research trials, community networks interested in the same study. This information may be stored on or written to the RFID tag of a reaction plate and/or a reagent container directly, or accessed from the network or network cloud.

The lab bench assistant or attached computer system may present a dashboard user interface for the analysis. The user may perform trend analysis on the results (example: quality control of the reagent by lot no., operator behavior etc.).

Using the lab bench assistant, the user may scan a pre-spotted plate and access relevant information for carrying out the analysis. The user may scan reagent containers and access relevant information for the reagent as it applies to the analysis. After the plate and/or reagent have been scanned, the user may assign samples and replicates to a multiplicity of reaction sites on the plate. The user may also operate a qPCR reaction calculator that suggests volumes and concentrations for reaction mixes based on the assays and reagents used in the analysis. The user may then be guided to perform the liquid, reagent, or sample transfers to the plate.

One option for performing liquid, reagent, or sample transfer utilizes an El-ClipTip™ Bluetooth™ Electronic Pipette. An El-ClipTip Pipette utilizes a digital pipetting protocol with a setup for the current designed plate that can be downloaded automatically into El-ClipTip Pipette to transfer the liquids, reagents, and samples efficiently. Another option is using a regular pipette where the user would be guided with voice and/or some visual indication on what volume of samples go on/into which reaction sites of the reaction plate.

In some embodiments, after a reaction plate is prepared, the user can schedule an instruments for their run protocol from location, including a remote location. In some embodiments, the user loads the reaction plate in the instrument and the analysis setup information is automatically downloaded by the instrument based on information provided by the reaction plate RFID tag. In some embodiments, the required run protocol may be automatically assigned to the reaction plate. Once the run is started, the user can monitor the results of the run from anywhere, and can perform quality control in real time as results are obtained.

After the run concludes, the instrument may push results to a cloud service. The user may access and review the results in the cloud. The user may perform further analysis by changing the settings for normalization, performing quality control, etc. The user may collaborate with others through the cloud service.

The overall system of smart instruments, smart consumables (including smart reaction plates and/or reagent containers), and a smart lab bench assistant may facilitate an integrated smart workflow for molecular analysis. The integrated smart workflow may eliminate the need to manually input data elements from consumables, reagents to instruments repetitively, and may thus make analysis less error prone. The integrated smart workflow for part of an analysis ecosystem can further include an El-ClipTip Pipette, an Electronic Laboratory Notebook (ELN), and/or a digital Laboratory Information Management System (LIMS).

In some additional embodiments, the instruments or the connected network cloud may include algorithms for the prediction of real time amplifications and results based on amplification curves (for example). Early prediction can reduce run times and improve results or repeated analysis. A trained model (e.g., based on machine learning from past analysis) may help detect the amplification process and thus reduce the need for tuning and correction.

Figure 2:
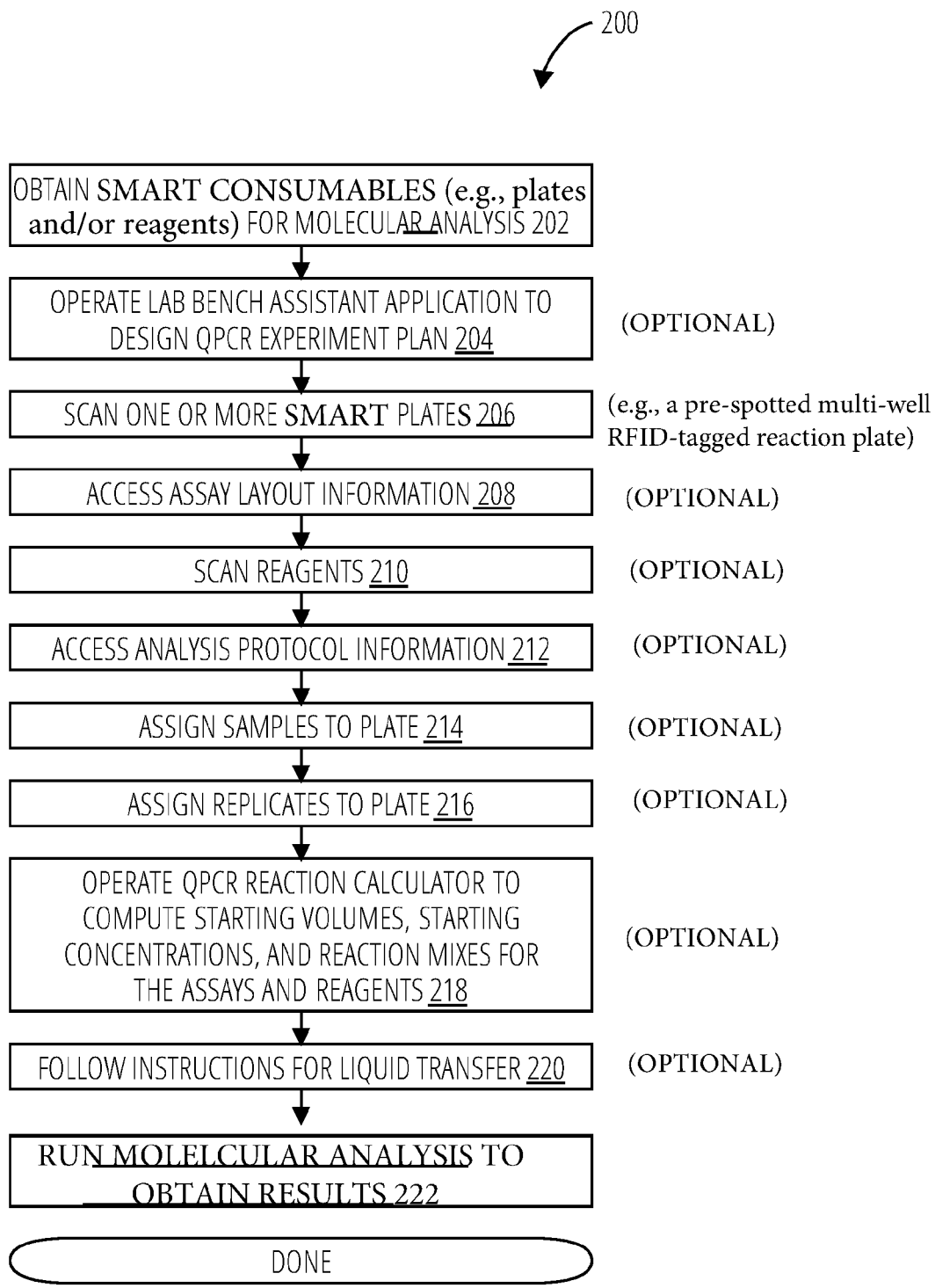
FIG. 2 illustrates a molecular analysis routine 200 in accordance with one embodiment.

Referring now to FIG. 2, a smart molecular analysis (qPCR in this non-limiting example) may begin by the user obtaining smart reagents, including for example reaction plates pre-spotted with a first reagent (e.g., an assay comprising one or more probes/primers) and/or reagents 202 contained in one or more reagent containers. Optionally, the user next operates the lab bench assistant application to design a qPCR analysis plan 204. In some embodiments, the user then scans one or more multi-well plates 206 to access assay reagents and layout information 208 (such as, for example, which reagents to use in a multiplicity of reaction sites) for the analysis.

In some embodiments, the user can then scan the reagents 210 to add to the plate by, for example, liquid transfer. In some embodiments, the user then accesses analysis protocol information 212 and assigns test samples to the plate 214.

Following these steps, the user, optionally, operates a qPCR reaction calculator to compute starting volumes, starting concentrations, and reaction mixes for the assays and reagents 218, and follows instructions for liquid transfer 220. After scanning a smart consumable, such as an RFID-tagged plate 206, and any other optional steps prior to or in between (e.g., 204,208,210,212,214,216,218,220), the reaction can be run by the instrument to produce molecular analysis results 222).

Figure 3:
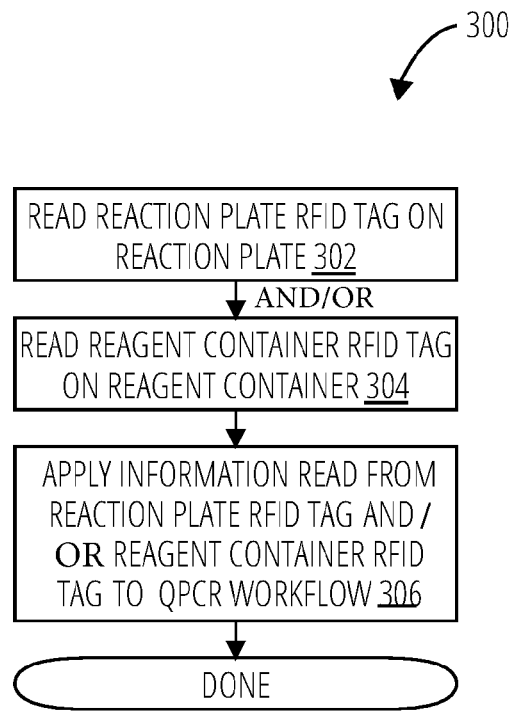
FIG. 3 illustrates another routine 300 for performing a molecular analysis in accordance with one embodiment.
Figure 4:
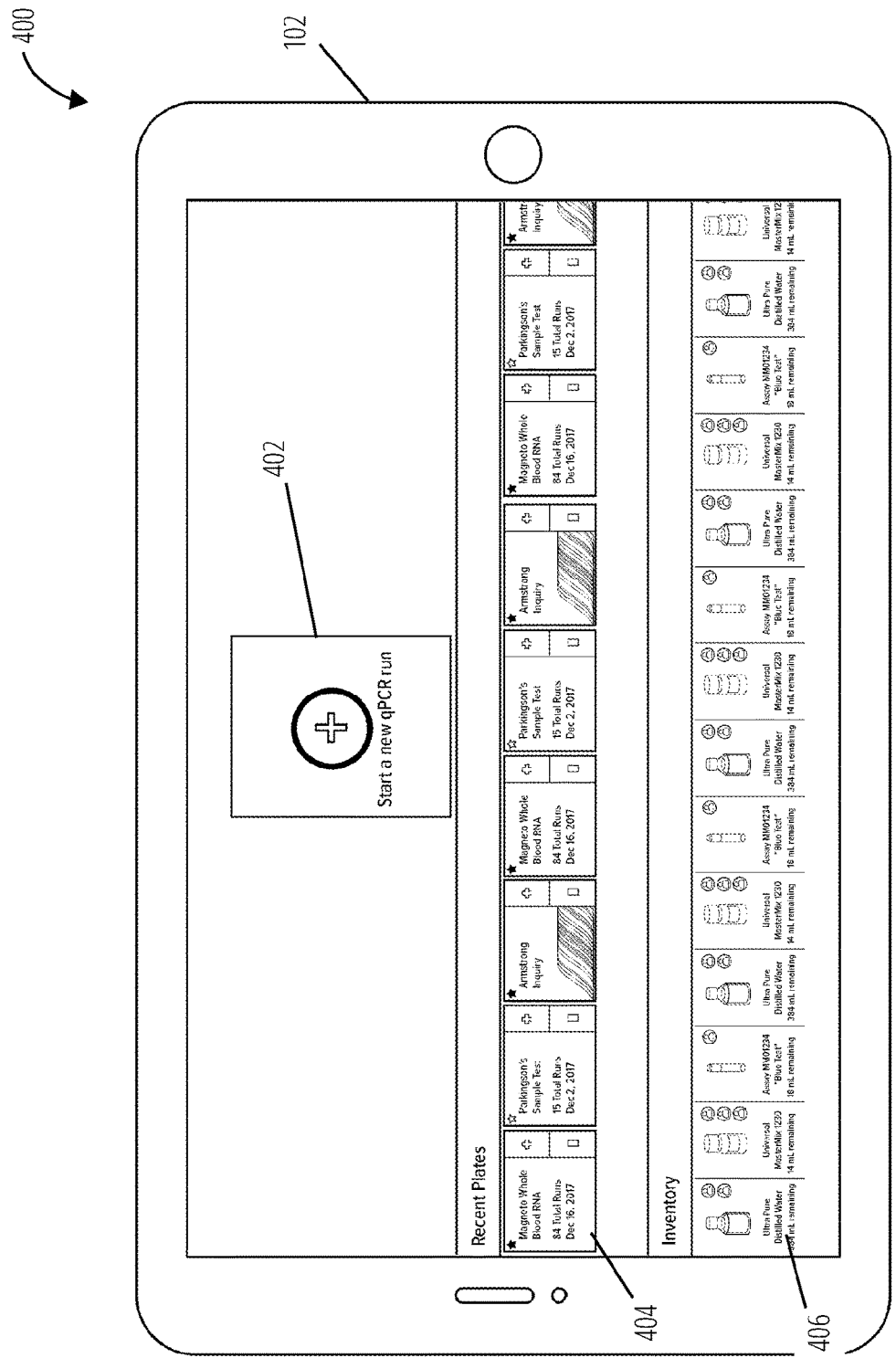
FIG. 4 illustrates a user interface 400 in accordance with one embodiment.
Figure 5:
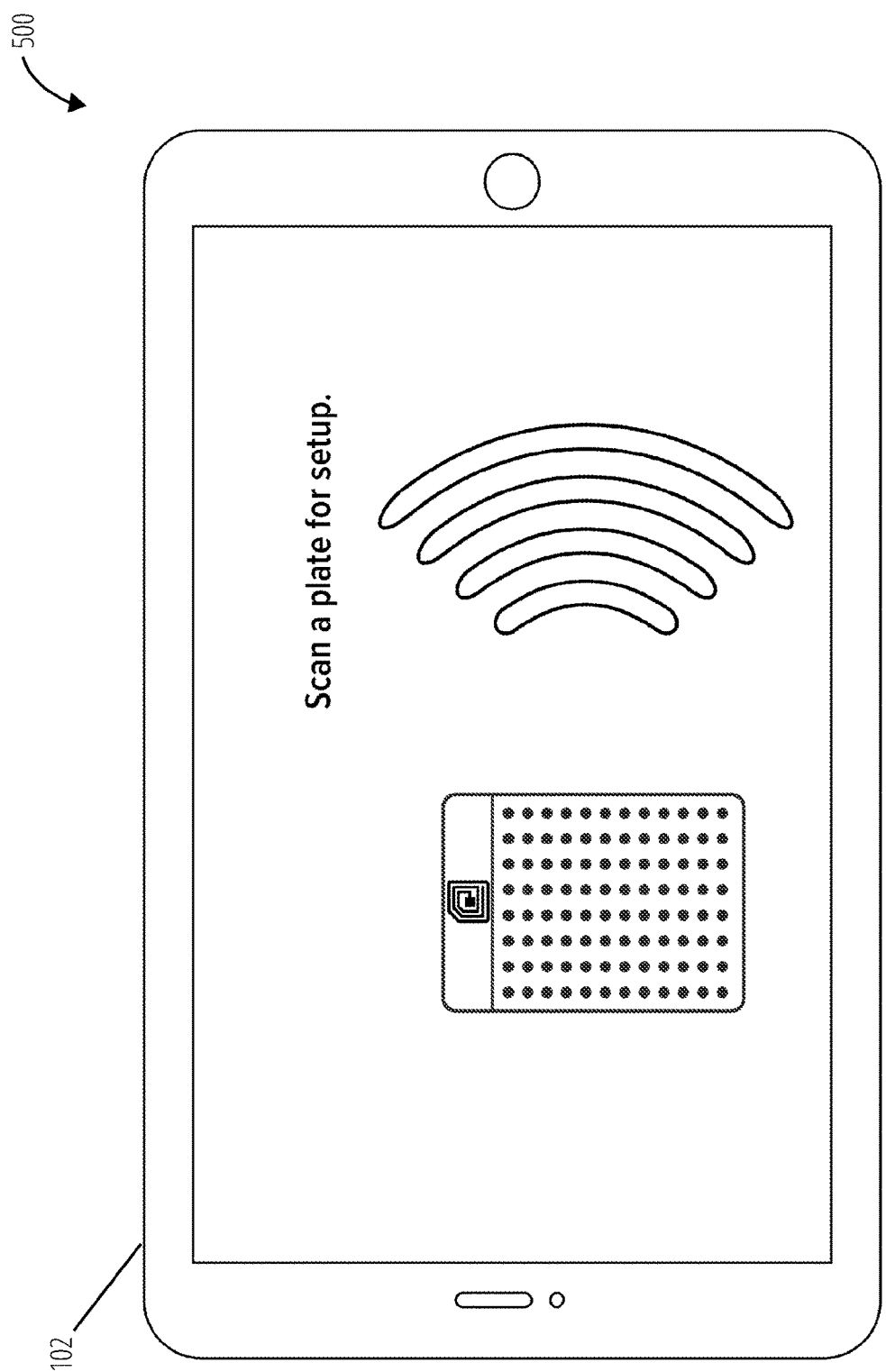
FIG. 5 illustrates a user interface 500 in accordance with one embodiment.
Figure 6:
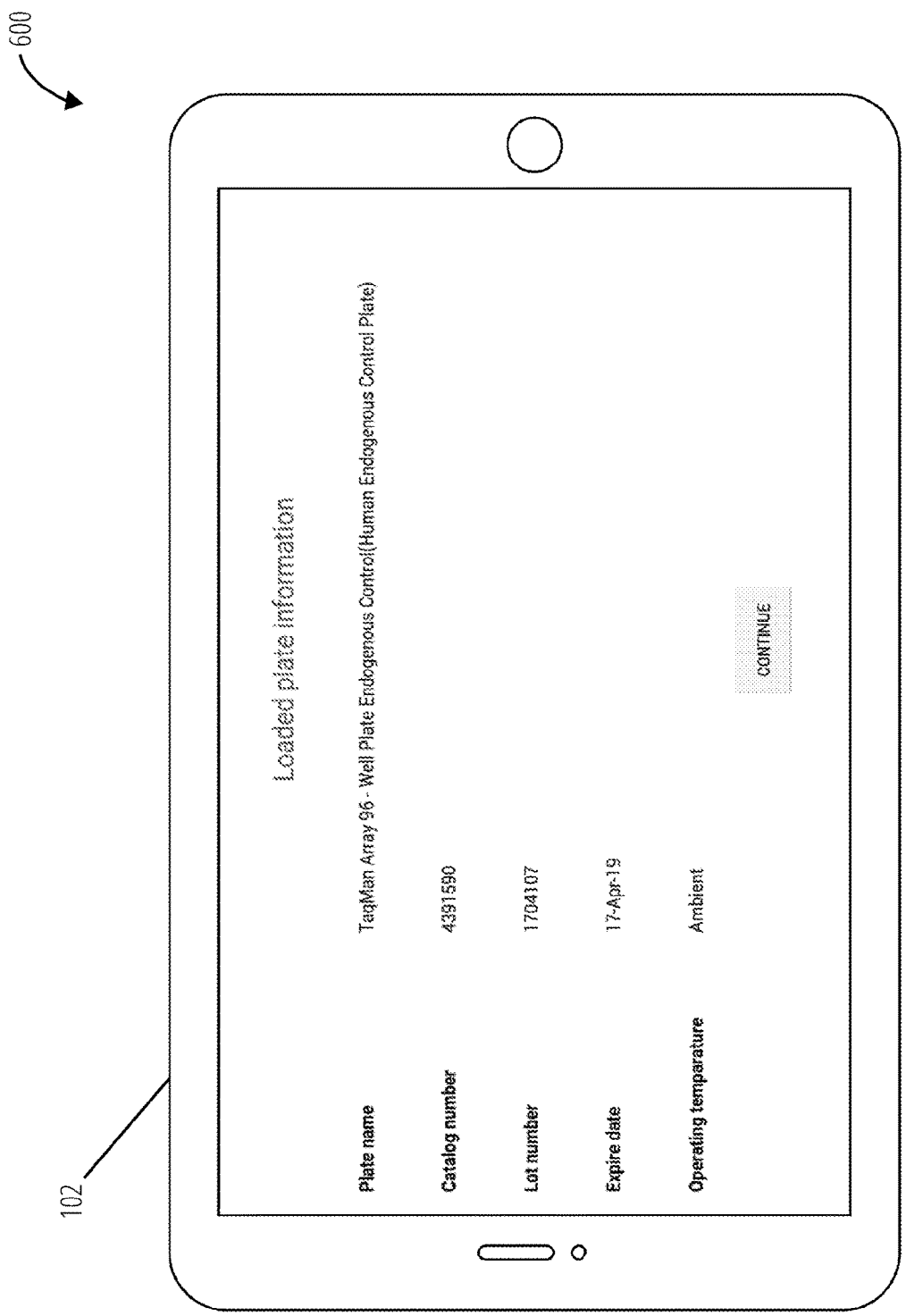
FIG. 6 illustrates a user interface 600 in accordance with one embodiment.
Figure 7:
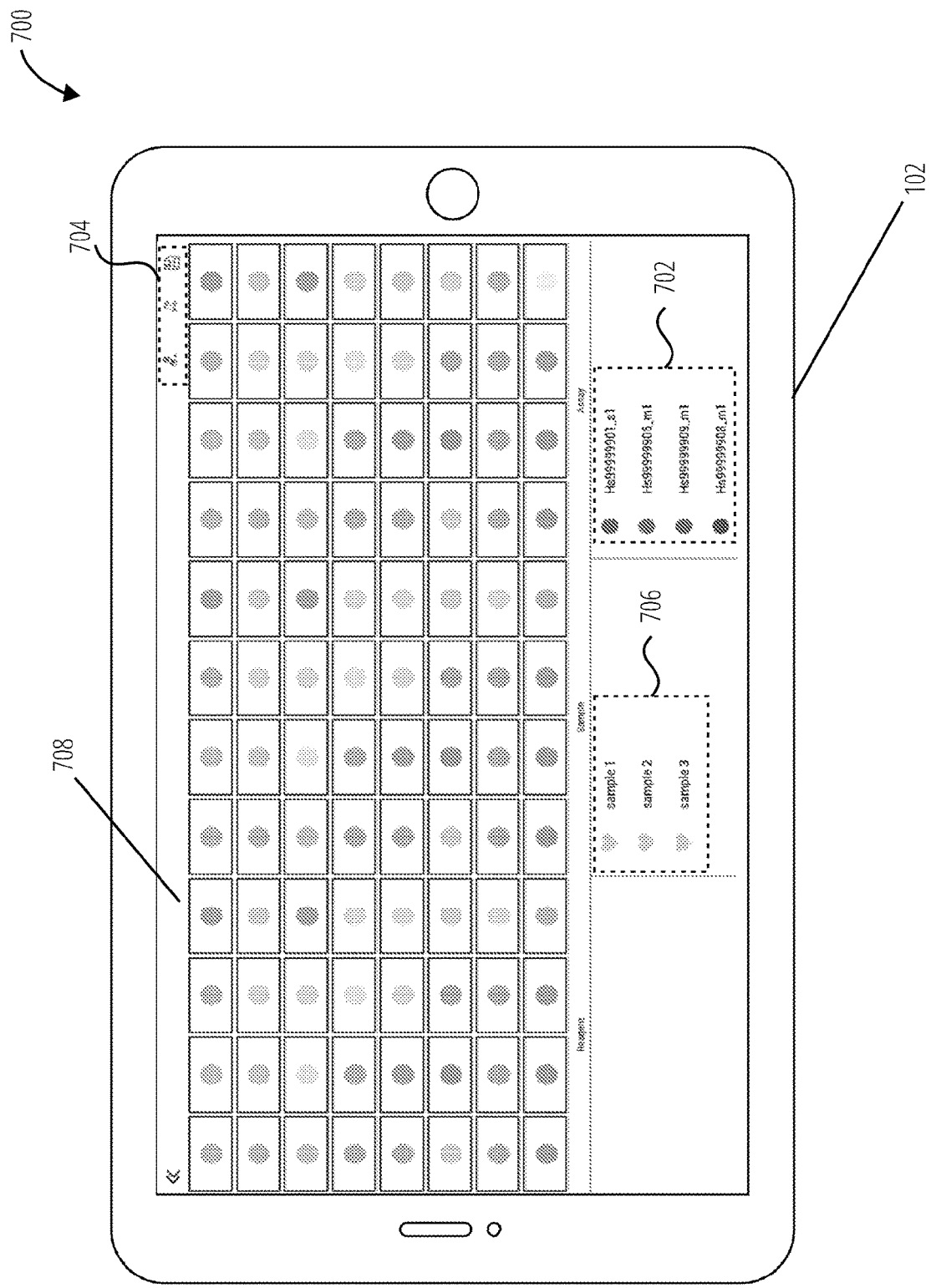
FIG. 7 illustrates a user interface 700 in accordance with one embodiment.
Figure 8:
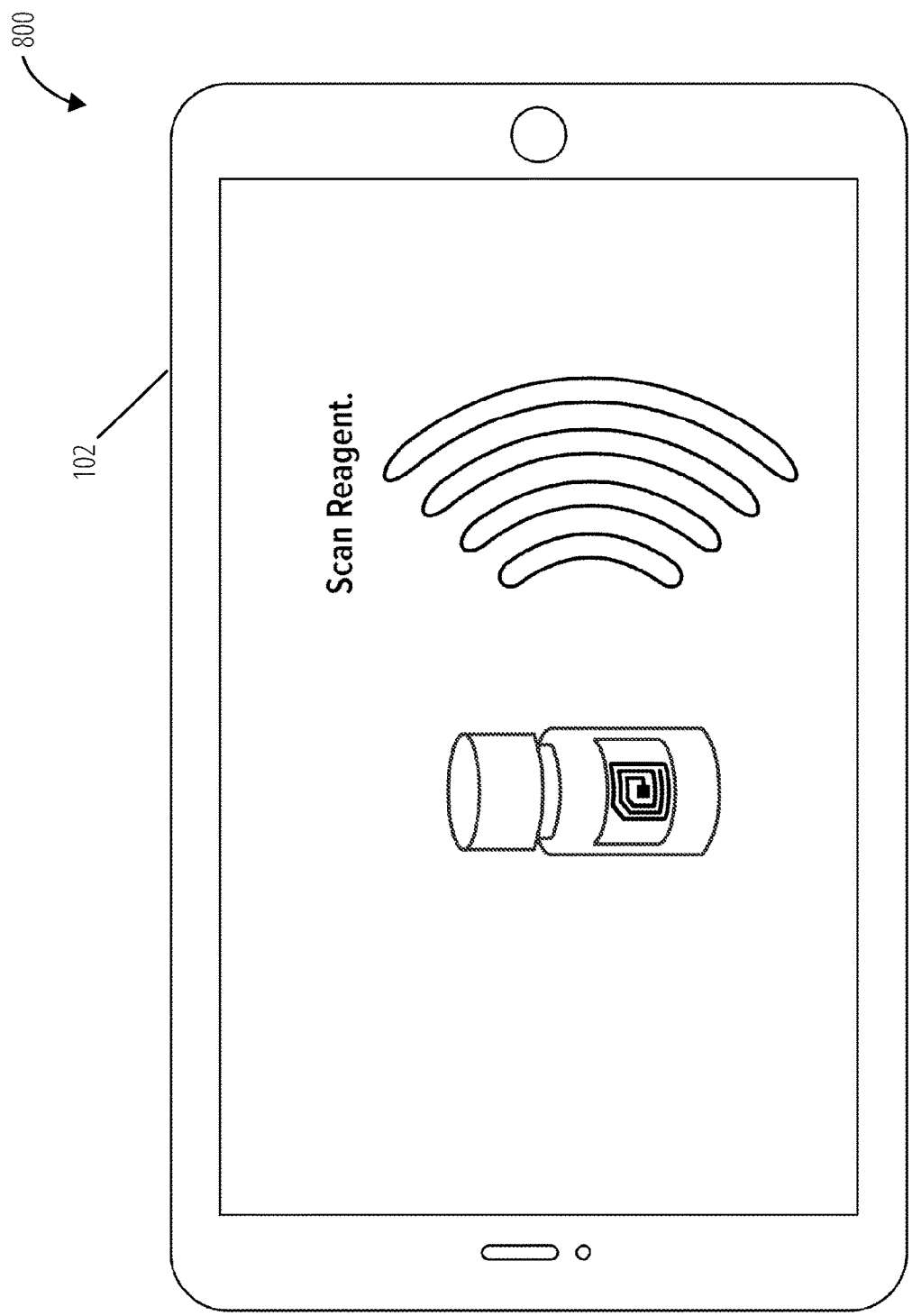
FIG. 8 illustrates a user interface 800 in accordance with one embodiment.
Figure 9:
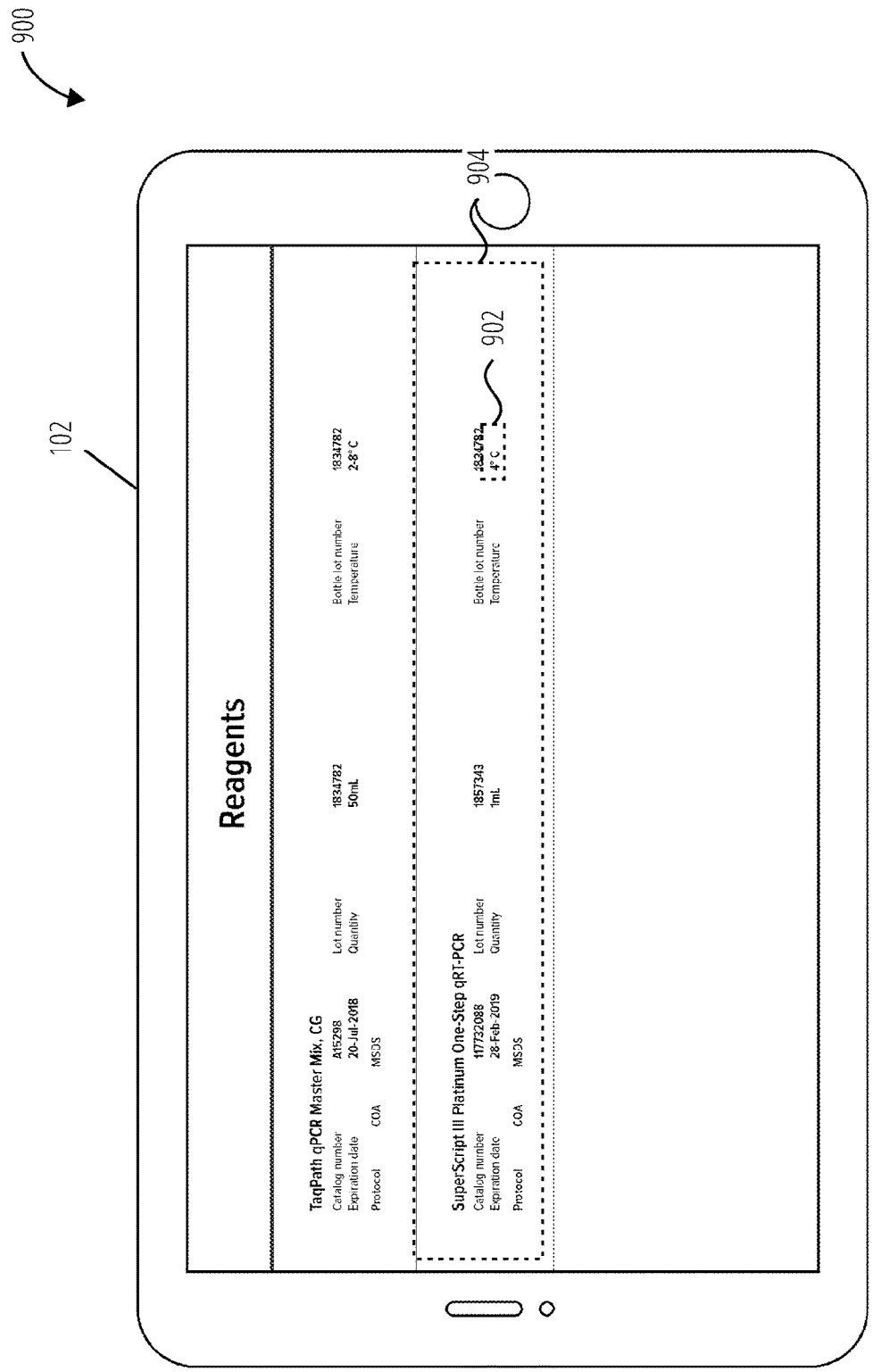
FIG. 9 illustrates a user interface 900 in accordance with one embodiment.
Figure 10:
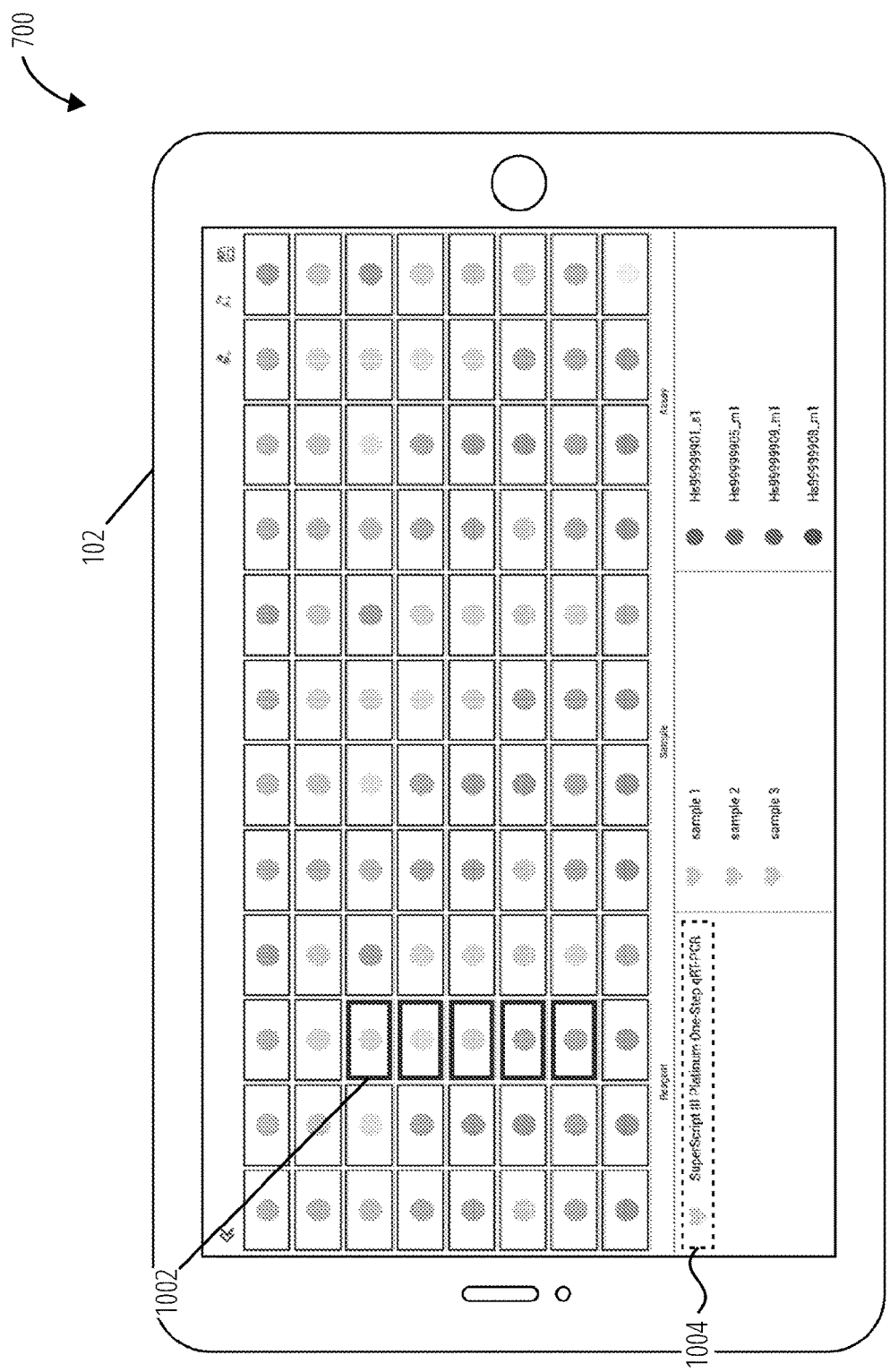
FIG. 10 illustrates a user interface 700 in accordance with one embodiment.

Referring now to FIG. 3, at block 302, an RFID tag on a reaction plate is read by an instrument and/or a lab bench assistant. In block 304, the instrument and/or lab bench assistant reads a reagent container RFID tag on a reagent container. In some embodiments, only the RFID tag on a reaction plate is read 302. In some other embodiments, only the RFID tag(s) on a reagent container(s) is read 304. In yet some other embodiments, both an RFID tag on a reaction plate and an RFID tag on a reagent container(s) are read 302 and 304. In block 306, the information read from either or both the RFID tag on a reaction plate and/or on one or more reagent container(s) is applied to facilitate a qPCR molecular analysis.

Referencing FIG. 4 through FIG. 10, a display device 102 may be utilized to show a variety of user interface screens to assist the user in configuring an analysis they wish to run on an instrument using system 100. These user interface elements are only one example of a smart user-driven molecular analysis that a lab bench assistant may utilize, and many others will be evident to those of ordinary skill in the art.

A user interface 400 may be displayed through the display device 102 showing a start icon 402, at least one reaction plate icon 404, and at least one inventory icon 406. The at least one reaction plate icon 404 may show recent reaction plates were utilized by a user. The reaction plate icon 404 may display information such as the name of the analysis that the reaction plate was being used for, the number of runs that were performed using the reaction plate, and a time stamp for the last instance that the reaction plate was utilized in an analysis.

An inventory icon 406 may provide information regarding consumables that are in the laboratory. The inventory icon 406 may include information such as the names of the consumable, the consumable ID number, an icon representing the type of the consumable, such as an assay, a reagent, or sample, the quantity of the consumable remaining in each specific substrate, holder, container, and the like, and icons identifying the last owners and current owners of the consumable in the laboratory. A user may select the inventory icon 406 to quickly locate the consumables that they wish to use in their analysis.

A start icon 402 may be provided to allow the user to start configuration of their analysis. When the start icon 402 is selected the display device 102 may display a user interface 500 prompting the user to scan a reaction plate RFID tag 122 of a reaction plate 116 they are going to be utilizing in their analysis.

After the reaction plate RFID tag 122 is scanned, a user interface 600 may be displayed through the display device 102. In some embodiments, the user interface 600 provides the user with specific information about the scanned plate such as the name, ID, part type, the production information (e.g., lot number, expiration date, etc.), order information (e.g., catalog number, cost, etc.), and certain properties such as operation and/or storage temperature. In some configurations, the user interface 600 may display information such as sensor history for the reaction plate such as temperature history, light exposure history, motion detection and/or shock history. After reviewing the information, the user may select to continue with configuration of the analysis by selecting a continue option displayed through the user interface 600.

The display device 102 displays a user interface 700 with a plate layout 708 corresponding to the positions of assays, reagents, and samples within a matrix of a plurality of reaction sites. When utilizing a pre-spotted plate, for example, the user interface 700 may display a matrix of reaction sites with a color coded indicator within each site. Then, in some embodiments, each color coded indicator may correspond to an assay displayed in a list of color coded assays 702 shown in the user interface 700. For non-spotted plates, a user may be able to configure the position of the assays they are using. This can be done, for example, by writing/rewriting information directly onto a reaction plate and/or reagent container RFID tag (e.g., using an RFID writer) and/or onto the cloud. While utilizing the user interface 700 a user may wish to assign a sample to the plate or a set of reaction sites. The user may interact with a set of icons 704 and a sample list 706 displayed within the user interface 700 to assign, edit, and save the configuration of the plate for use in the instrument. The icons 704 of the user interface 700 may allow the user to scan a reagent container RFID tag 110 for a reagent they would like to add to the reaction plate.

The user interface 800 shows a notification to the user that they are able to use the RFID reader 124 of the display device to scan a reaction plate RFID tag 122 and/or a reagent container RFID tag 110. In some configurations, a user may be able to scan multiple reaction plate RFID tags and/or reagent container RFID tags that they wish to use with the system 100.

The user interface 900 shows a list of scanned reagent information 904 that includes properties, production information, and sensor history information such as temperature history 902.

The display device 102 may return back to displaying user interface 700 after the reagents have been scanned. The user interface 700 displays a reagent icon 1004 for each reagent that was scanned or selected for by the user. The user interface 700 may display indicators 1002 identifying specific reaction sites for the user to transfer the reagent into in accordance with the protocol utilized in the analysis.

Figure 11:
FIG. 11 illustrates a user interface 1100 in accordance with one embodiment.
Figure 12:
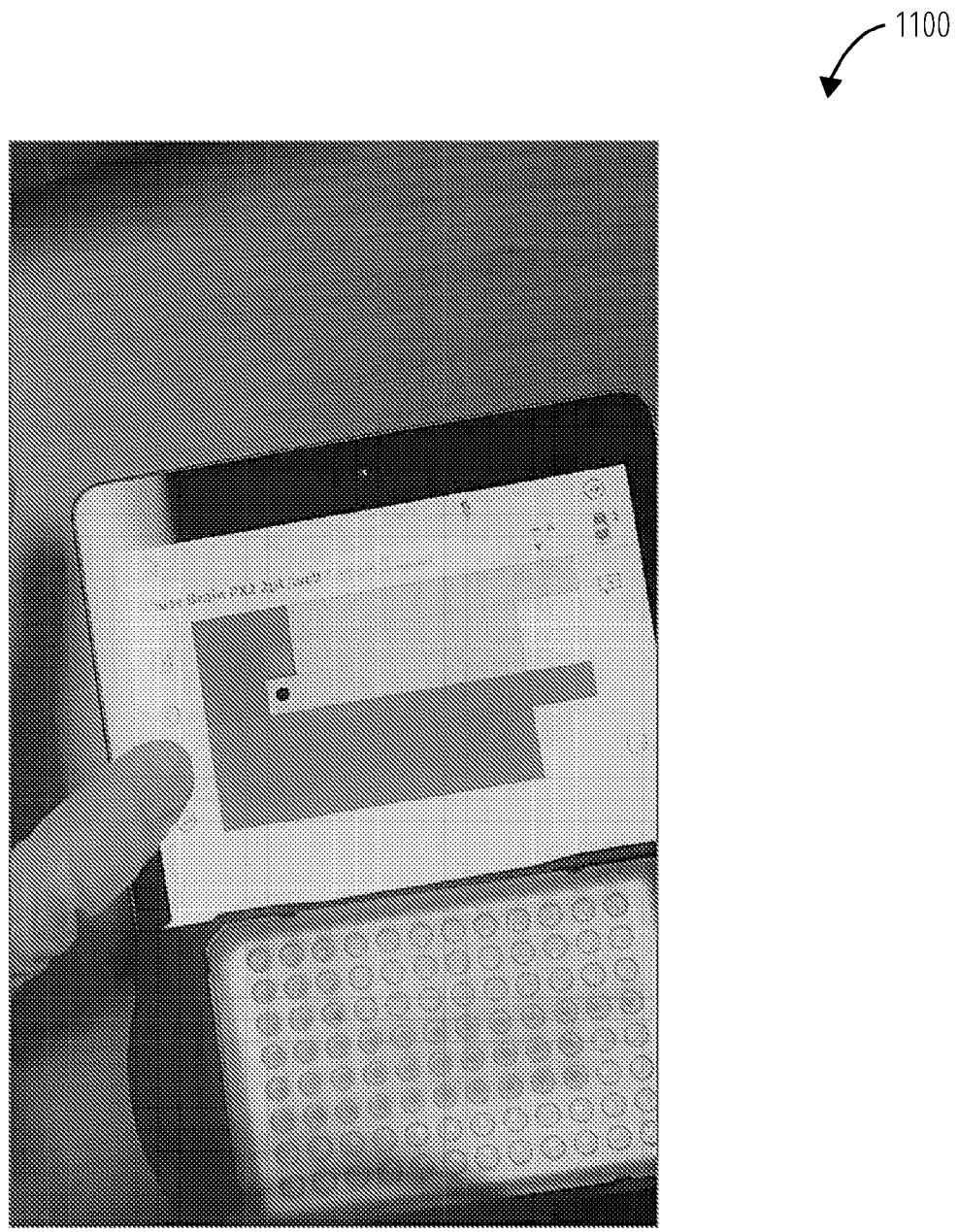
FIG. 12 further illustrates a user interface 1100 in accordance with one embodiment.

FIG. 11 and FIG. 12 show photographs of a user configuring a reaction plate through user interface 1100. The user may indicate the location of the assays, samples, and/or reagents that they position within each reaction site of the reaction plate.

Figure 13:
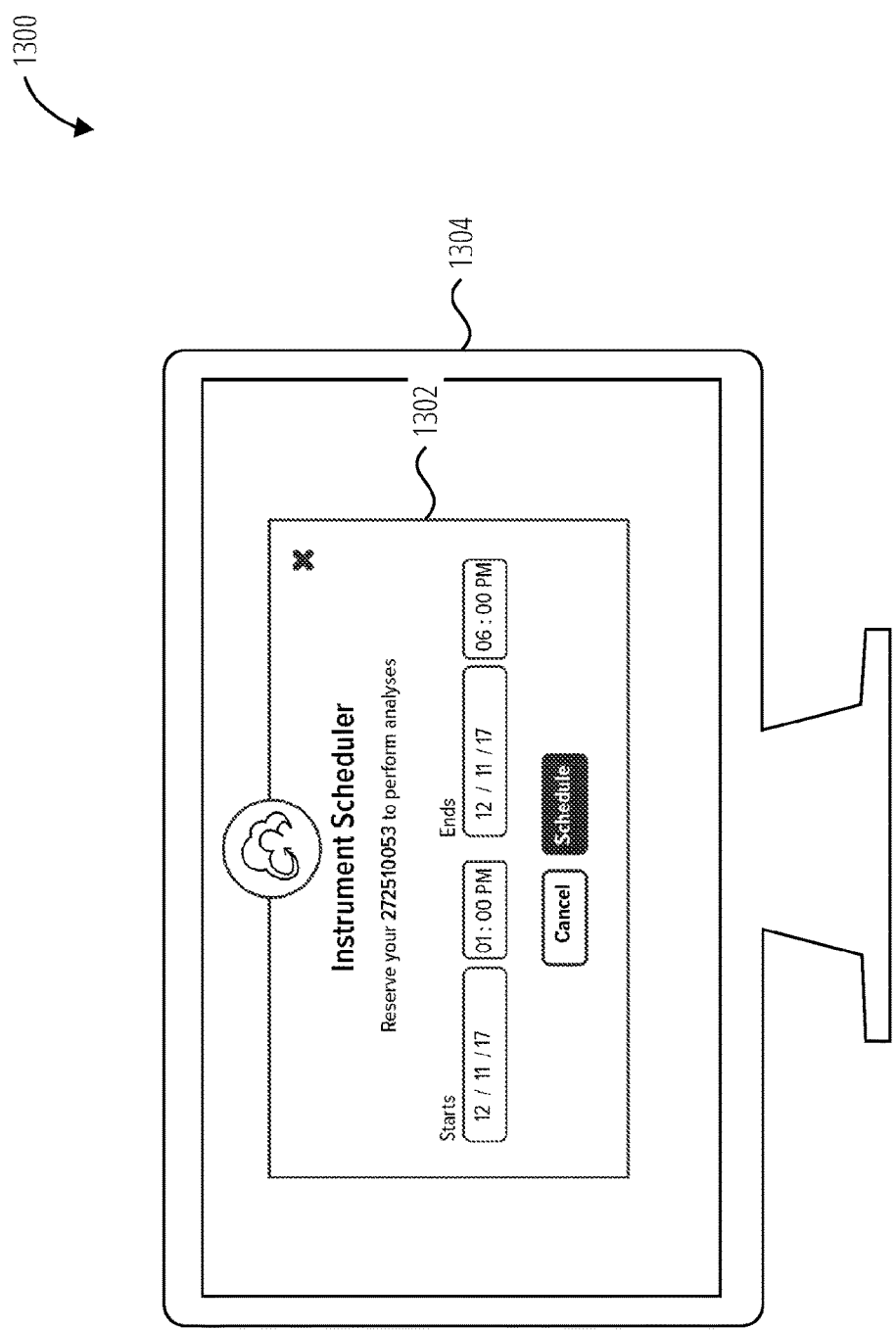
FIG. 13 illustrates a user interface 1300 in accordance with one embodiment.

FIG. 13 shows a user interface 1300 displaying an instrument scheduler 1302 displayed to a user through a display device 1304 of a personal computer/work station. After a reaction plate has been configured, for example, a user may utilize the user interface 1300 to view an instrument scheduler 1302 for the availability of the instrument that they wish to run their analysis on. In some embodiments, the instrument scheduler 1302 may allow the user to set the date and time that they wish to perform their analysis.

Figure 14:
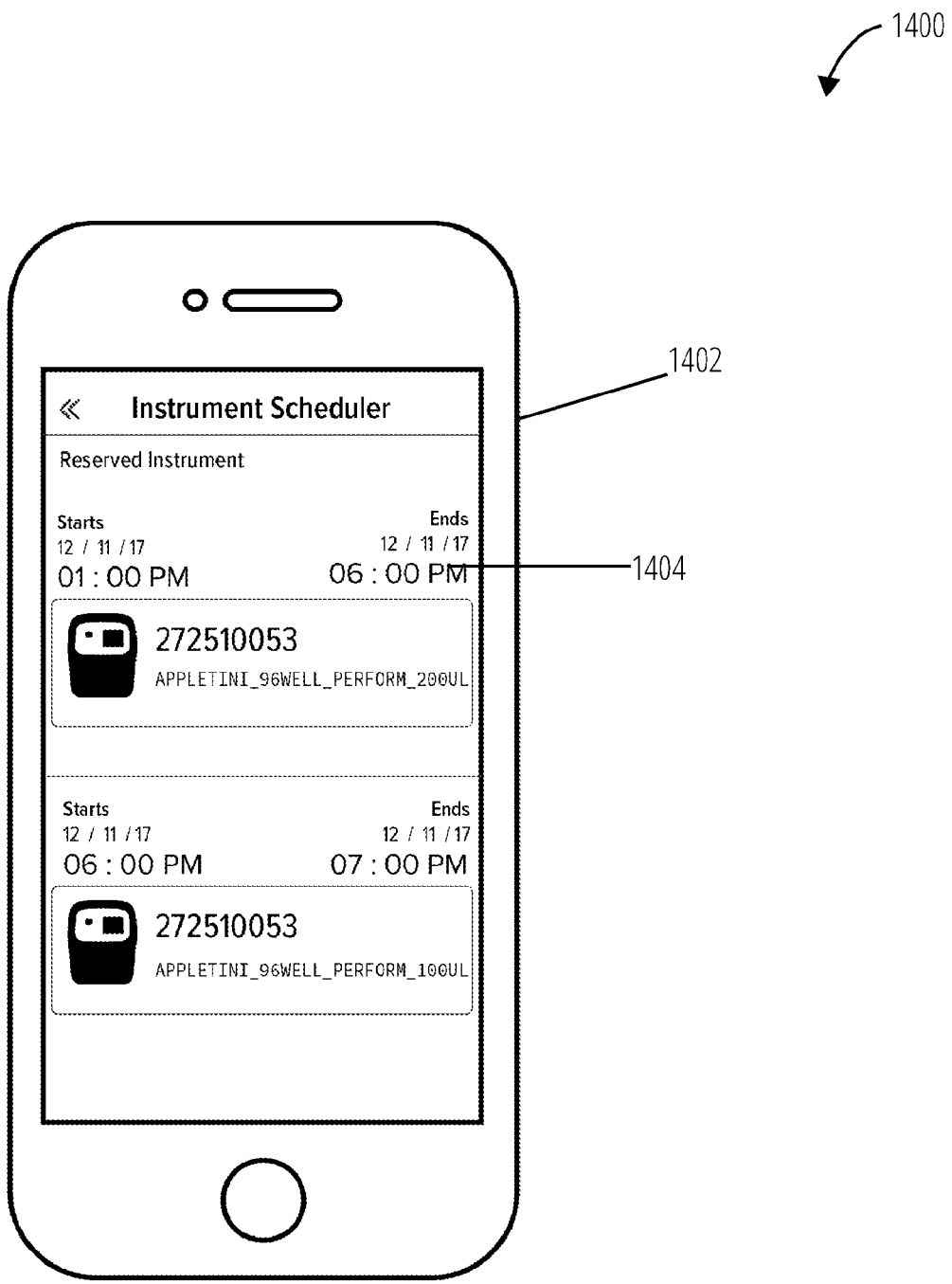
FIG. 14 illustrates a user interface 1400 in accordance with one embodiment.
Figure 15:
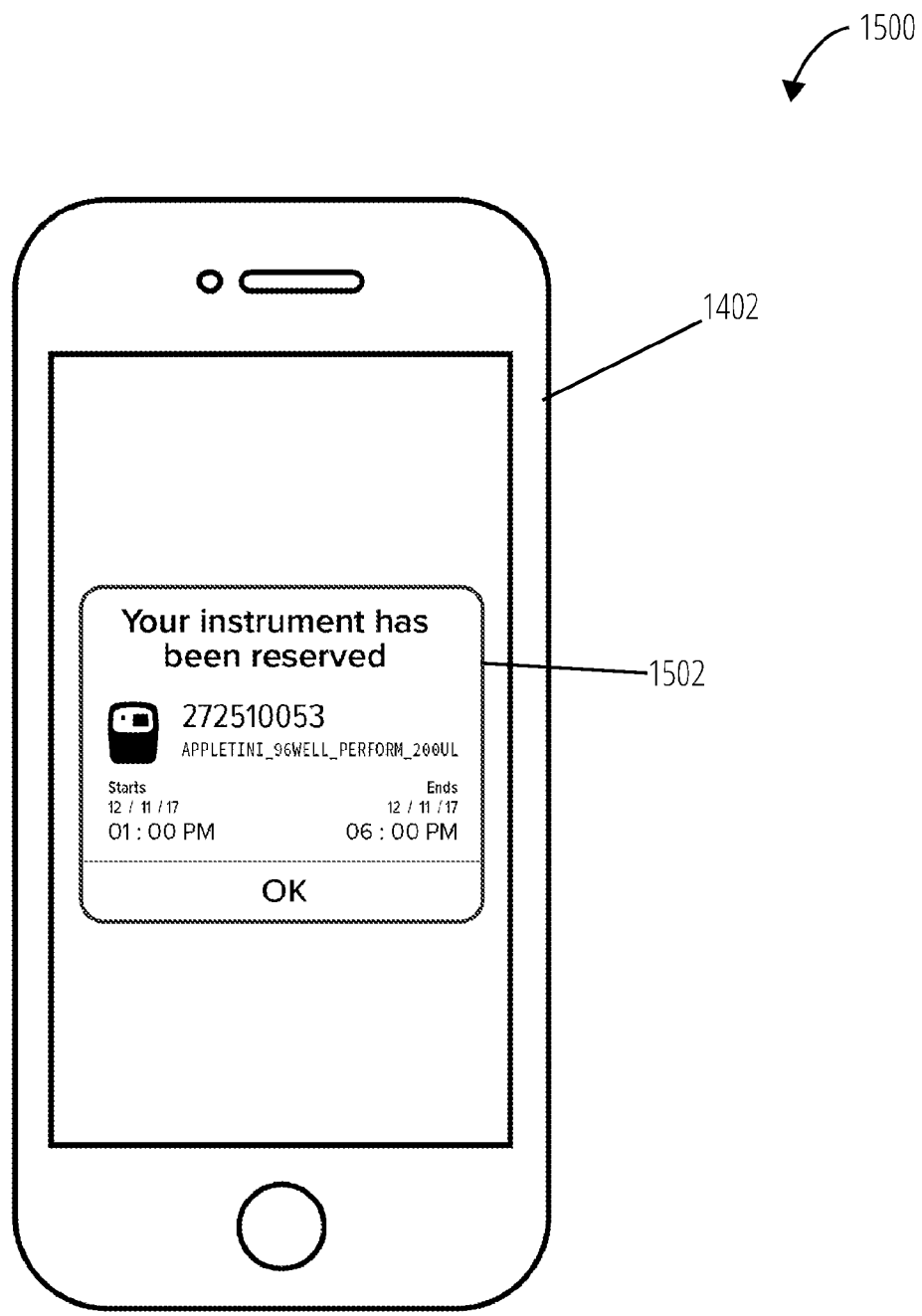
FIG. 15 illustrates a user interface 1500 in accordance with one embodiment.
Figure 16:
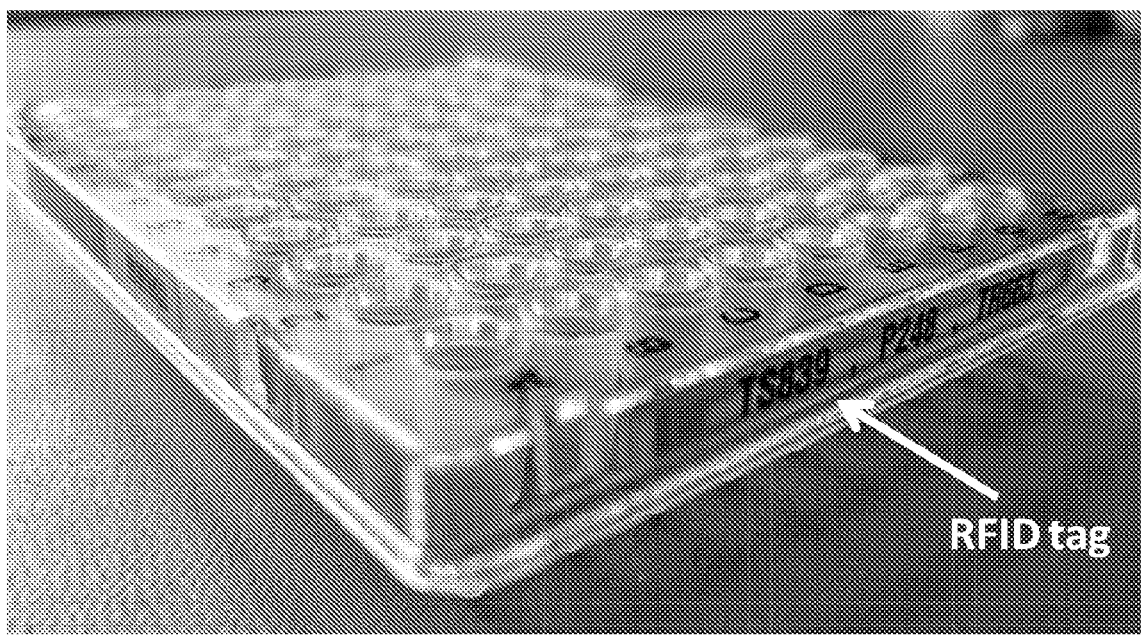
FIG. 16 illustrates an RFID-tagged, multi-well reaction plate in accordance with one embodiment.

Referencing FIG. 14 and FIG. 15, a user may schedule or view a list of their scheduled analyses on an instrument through a mobile device such as display device 1402. The display device 1402 may allow the use to view the scheduler entry 1404 showing the scheduled runs for the instrument. The display device 1402 may also show the user a scheduler notification 1502 after they have scheduled the instrument and a reminder to begin an experiment.

"Logic" herein refers to machine memory circuits, non-transitory machine readable media, and/or circuitry which by way of its material and/or material-energy configuration comprises control and/or procedural signals, and/or settings and values (such as resistance, impedance, capacitance, inductance, current/voltage ratings, etc.), that may be applied to influence the operation of a device. Magnetic media, electronic circuits, electrical and optical memory (both volatile and nonvolatile), and firmware are examples of logic. Logic specifically excludes pure signals or software per se, however it does not exclude machine memories comprising software and thereby forming configurations of matter.

What is claimed is:

1. A system for performing a molecular analysis having a molecular analysis workflow including a reagent application instruction and a reagent mixing instruction, the system comprising:
 a reagent container for containing a first reagent and comprising a reagent container radio frequency identification RFID tag; and
 a reaction plate comprising:
  a plurality of reaction sites; and
  a reaction plate radio frequency identification RFID tag, the reaction plate configured to accommodate simultaneous performance of multiple assays, wherein the reagent container RFID tag or the reaction plate RFID tag or both includes stored the molecular analysis workflow including the reagent application instruction and the reagent mixing instruction, the reagent application instruction for directing application of particular volumes of the first reagent contained within the reagent container to one or more reaction sites spotted with a second reagent of the plurality of reaction sites of the reaction plate, each reaction site of the one or more reaction sites having an amount of the second reagent spotted on each reaction site, wherein the reaction plate RFID tag includes stored identification information for identifying the one or more reaction sites spotted with the second reagent the reaction plate RFID tag or the reagent container RFID tag or both includes stored the reagent mixing instruction for mixing the amount of the second reagent spotted on a corresponding reaction site and a particular volume of the first reagent applied to the corresponding reaction site.

2. The system of claim 1, wherein the system is configured to perform one or more polymerase chain reaction PCR assays.

3. The system of claim 1, wherein the reaction plate or the reagent container or both further comprises a temperature sensor coupled to the reaction plate RFID tag or to the reagent container RFID tag or both, the reaction plate RFID tag or the reagent container RFID tag or both capable of storing a reaction plate temperature history or a reagent container temperature history.

4. The system of claim 1, wherein the reaction plate or the reagent container or both further comprises a light sensor coupled to the reaction plate RFID tag or to the reagent container RFID tag or both, the reaction plate RFID tag the reagent container RFID tag or both capable of storing a reaction plate light exposure history or a reagent container light exposure history.

5. The system of claim 1, wherein the reaction plate or the reagent container or both comprises a motion sensor coupled to the reaction plate RFID tag or to the reagent container RFID tag or both, the reaction plate RFID tag or the reagent container RFID tag or both capable of storing a reaction plate motion detection history or a reagent container motion detection history.

6. The system of claim 1, further comprising:
 an instrument comprising an RFID tag reader operable to read the molecular analysis workflow from the reagent container RFID tag and the reagent plate RFID tag.

7. A method of using the system of claim 1, the method comprising:
 reading the reaction plate RFID tag;
 reading the reagent container RFID tag; and
 performing the molecular analysis.

8. The method of claim 7 wherein the reagent container RFID tag further includes stored identifying information relative to the first reagent contained within the reagent container, and the reaction plate RFID tag further includes stored plate layout information associating one or more assays of the multiple assays with one or more reaction sites of the plurality of reaction sites of the reaction plate; and wherein
the reaction plate RFID tag is configured to store a usage rate of the particular volumes of the first reagent applied to the plurality of reaction sites.

9. The method of claim 8,
wherein the reaction plate RFID tag includes stored reagent identification information of corresponding reagents for applying to each reaction site of the plurality of reaction sites, at least two reaction sites of the plurality of reaction sites comprising different reagents, the method further comprising reading the reagent identification information from the reaction plate RFID tag.

10. The system of claim 1, further comprising:
an RFID tag reader operable to read the reaction plate RFID tag and the reagent container RFID tag; and
a display device communicatively connected to the RFID tag reader, wherein the reaction plate RFID tag includes a reaction plate layout displaying instruction that, when read by the RFID tag reader, causes the display device to display a plate layout representative of the reaction plate, and wherein the reagent container RFID tag includes stored a location instruction that, when read by the RFID tag reader, causes the display device to indicate, on the plate layout displayed, one or more specific reaction sites to which to transfer the particular volumes of the first reagent contained in the reagent container.

11. The system of claim 10, wherein the reagent container RFID tag further includes a reagent volume instruction for identifying a particular volume of the reagent to add to the one or more specific reaction sites of the reaction plate.

12. The system of claim 1, wherein the reagent container RFID tag or the reaction plate RFID tag or both includes a reagent transfer instruction for directing transfer of particular amounts of the first reagent contained in the reagent container to a specified subset of the reaction sites.

13. The system of claim 1, wherein the reaction plate RFID tag includes stored;
plate layout information associating one or more assays of the multiple assays with one or more reaction sites of the reaction plate, and
the reaction plate RFID tag is configured to store a usage rate of the amount of the first reagent applied to the plurality of reaction sites.

* * * * *